US006093725A

United States Patent [19]

Cook et al.

[11] Patent Number: 6,093,725

[45] Date of Patent: Jul. 25, 2000

[54] FRANGIBLE COMPOUNDS FOR PATHOGEN INACTIVATION

[75] Inventors: David Cook, Lafayette; John E. Merritt, Walnut Creek; Aileen Nerio, Fremont; Henry Rapoport, Berkeley; Adonis Stassinopoulos, Dublin; Susan Wollowitz, Walnut Creek, all of Calif.; Jan Matejovic, Toronto, Canada

[73] Assignee: Cerus Corporation, Concord, Calif.

[21] Appl. No.: 09/003,115

[22] Filed: Jan. 6, 1998

Related U.S. Application Data

[63] Continuation-in-part of application No. 08/779,885, Jan. 6, 1997, abandoned, and a continuation-in-part of application No. 08/779,830, Jan. 6, 1997, abandoned.

[60] Provisional application No. 60/043,696, Apr. 15, 1997.

[51] Int. Cl.[7] ........................ A61K 31/44; C07D 219/08

[52] U.S. Cl. ............................................ 514/297; 546/106

[58] Field of Search ............................ 546/106, 23, 105; 514/297

[56] References Cited

U.S. PATENT DOCUMENTS

| | | |
|---|---|---|
| 4,337,269 | 6/1982 | Berke et al. . |
| 4,833,165 | 5/1989 | Louderback . |
| 5,399,719 | 3/1995 | Wollowitz et al. . |
| 5,559,250 | 9/1996 | Cook et al. . |
| 5,691,371 | 11/1997 | Denny et al. . |

FOREIGN PATENT DOCUMENTS

| | | |
|---|---|---|
| 40323/95 | 6/1996 | Australia . |
| 4444045 | 6/1996 | Germany . |
| WO 94/20090 | 9/1994 | WIPO . |
| WO 96/14737 | 5/1996 | WIPO . |
| WO 96/39818 | 12/1996 | WIPO . |
| WO 96/40857 | 12/1996 | WIPO . |
| WO 97/02028 | 1/1997 | WIPO . |
| WO 97/07674 | 3/1997 | WIPO . |
| WO 97/21346 | 6/1997 | WIPO . |

OTHER PUBLICATIONS

Derwent World Patent Index Record for Patent Family of DE 4444045, 1998.

Gourdie, et al., "DNA–Directed Alkylating Agents. 1. Structure–Activity Relationships for Acridine–Linked Aniline Mustards: Consequences of Varying the Reactivity of the Mustard," J. Med. Chem., vol. 33(4):1177–1186 (1990).

Cates, L.A. et al., (1984) "Phosphorous–Nitrogen Compounds. 24. Phosphoramide Mustard Carrier Derivatives" *J. Med. Chem.* 27(3):397–401.

Hanson et al., "Application of a Rapid Microplaque Assay for Determination of Human Immunodeficiency Virus Neutralizing Antibody Titers," *J. Clin. Micro.,* (1990) 28:2030–2034.

Hogman et al., "Storage of saline–adenine–glucose–mannitol–suspended red cells in a new plastic container: polyvinylchloride plasticized with butyryl–n–trihexyl–citrate," *Transfusion,* (1991) 31:26–29.

Hogman et al., "Half–Strength Citrate CPD Combined with a New Additive Solution for Improved Storage of Red Blood Cells Suitable for Clinical Use," *Vox Sang,* (1993) 65:271–278.

Horowitz et al., "Solvent/Detergent–Treated Plasma: A virus–Inactivated Substitute for Fresh Frozen Plasma," *Blood,* (1992) 79:826–831.

Horowitz et al., "Inactivation of viruses in labile blood derivatives," *Transfusion,* (1985) 25:516–522.

LoGrippo et al., "Chemical and Combined Methods for Plasma Sterilization," *Proceedings of the Sixth Congress of the International Society of Blood Transfusion,* Bibliotheca Haematologica (Hollander, ed.) 1958, pp. 225–230.

Mattes et al., "GC–rich regions in genomes as targets for DNA alkylation" *Carcinogenesis* (1988) 9:2065–2072.

Mullman et al., "Guidelines for Prevention of Transmission of Human Immunodeficiency Virus and Hepatitis B Virus to Health–Care and Public–Safety Workers," *Morbidity and Mortality Weekly Report,* (1989) 38:3–6.

Peck et al., "Nitrogen Mustard Analogs of Antimalarial Drugs," *J. Amer. Chem. Soc.,* (1959) 81:3984–3989.

Piquet et al., "Virus Inactivation of Fresh Frozen Plasma by a Solvent Detergent Procedure: Biological Results," *Vox Sang.* (1992) 63:251–256.

Popovic et al., "Detection, Isolation, and Continuous Production of Cytopathic Retroviruses (HTLV–III) from Patients with AIDS and Pre–AIDS," *Science,* (1984) 224:497–500.

Wagner et al., "Red cell alterations associated with virucidal methylene blue phototreatment," *Transfusion,* (1993) 33:30–36.

Wagner et al., "Differential sensitivities of viruses in red cell suspensions to methylene blue photosensitization," *Transfusion,* (1994) 34:521–526.

Beutler et al., "The Role of Bone Marrow Transplantation in the Treatment of Acute Leukemia in Remission," *Blood,* (1982) 59:1115–1117.

Cummings et al., "Determination of reactive nitrogen mustard anticancer drugs in plasma by high–performance liquid chromatography using derivatization" *Anal. Chem.* (1991) 63(15):1514–1519.

Davey et al., "The Effect of Prestorage Irradiation on Posttransfusion Red Cell Survival," *Transfusion,* (1992) 32:525–528.

Gravatt et al., "DNA–directed alkylating agents. 4. 4–anilinoquinoline–based minor groove directed aniline mustards" *J. Med. Chem.* (1991) 34:1552–1560.

Greenwalt et al., "Studies in Red Blood Cell Preservation," *Vox Sang,* (1990) 58:94–99.

*Primary Examiner*—Deborah C. Lambkin
*Attorney, Agent, or Firm*—Morrison & Foerster

[57] ABSTRACT

Compounds and methods for inactivating pathogens in materials are described, including compositions and methods for inactivating pathogens in biological materials such as red blood cell preparations and plasma. The compounds and methods may be used to treat materials intended for in vitro or in vivo use, such as clinical testing or transfusion. The compounds are designed to specifically bind to and react with nucleic acid, and then to degrade to form breakdown products. The degradation reaction is preferably slower than the reaction with nucleic acid.

46 Claims, No Drawings

FRANGIBLE COMPOUNDS FOR PATHOGEN INACTIVATION

CROSS-REFERENCE TO RELATED APPLICATIONS

This application claims the benefit of U.S. Provisional application Ser. No. 60/043,696, filed Apr. 15, 1997, the disclosure of which is incorporated herein by reference.

This application also is a continuation-in-part of U.S. patent application Ser. No. 08/779,885, filed Jan. 6, 1997, abandoned; and is a continuation-in-part of U.S. patent application Ser. No. 08/779,830, filed Jan. 6, 1997, abandoned, the disclosures of which are incorporated herein by reference.

STATEMENT OF RIGHTS TO INVENTIONS MADE UNDER FEDERALLY SPONSORED RESEARCH

This invention was made with United States government support under Grant 1-RO1-HL53380 from the NHLBI. The United States Government has certain rights in this invention.

TECHNICAL FIELD

This invention relates to compounds which are useful for inactivating pathogens in a material, such as a blood product, and to methods of use of the compounds.

BACKGROUND ART

The transmission of disease by blood products and other biological materials remains a serious health problem. While significant advances in blood donor screening and blood testing have occurred, viruses such as hepatitis B (HBV), hepatitis C (HCV), and human immunodeficiency virus (HIV) may escape detection in blood products during testing due to low levels of virus or viral antibodies. In addition to the viral hazard, there are currently no licensed tests to screen for the presence of bacteria or protozoans in blood intended for use in transfusions. The risk also exists that a hitherto unknown pathogen may become prevalent in the blood supply and present a threat of disease transmission, as in fact occurred before the recognition of the risk of HIV transmission via blood transfusions.

Exposure of laboratory workers to blood or other body fluids also presents a health hazard. Twelve thousand health-care workers whose jobs involve exposure to blood are infected with hepatitis B virus each year, according to estimates from the Centers for Disease Control ("Guidelines for Prevention of Transmission of Human Immunodeficiency Virus and Hepatitis B Virus to Health-Care and Public-Safety Workers," Morbidity and Mortality Weekly Report, vol. 38, no. S-6, June 1989).

Several methods have been proposed to complement donor screening and blood testing to decrease the incidence of disease due to transfusions. The introduction of chemical agents into blood or blood plasma has been suggested to inactivate pathogens prior to clinical use of the blood product. Nitrogen mustard, $CH_3—N(CH_2CH_2Cl)_2$, was added to blood components in an investigation of potential virucidal agents. However, substantial hemolysis occurred at the concentrations necessary to inactivate one of the viruses studied, rendering nitrogen mustard unsuitable for use in blood. LoGrippo et al., Proceedings of the Sixth Congress of the International Society of Blood Transfusion, Bibliotheca Haematologica (Hollander, ed.), 1958, pp. 225–230.

A "solvent/detergent" (S/D) method for inactivating viruses was described in Horowitz et al., *Blood* 79:826 (1992) and in Horowitz et al., *Transfusion* 25:516 (1985). This method utilized 1% tri(n-butyl)phosphate and 1% Triton X-100 at 30° C. for 4 hours to inactivate viruses in fresh frozen plasma. Piquet et al., Vox Sang. 63:251 (1992), used 1% tri(n-butyl)phosphate and 1% Octoxynol-9 to inactivate viruses in fresh frozen plasma. Another method for inactivating viruses in blood involves the addition of phenol or formaldehyde to the blood. U.S. Pat. No. 4,833,165. However, both the solvent/detergent method and the phenol/formaldehyde method require removal of the chemical additives prior to clinical use of the blood product.

Inactivation of pathogens in blood products using photoactivated agents has also been described; see, e.g., Wagner et al., *Transfusion,* 34:521 (1994). However, due to the absorption of light by hemoglobin in several regions in the ultraviolet and visible spectrum, phototreatment is limited in its application to materials containing red blood cells. There is also some indication that phototreatment of red blood cells alters the cells in some manner; see Wagner et al., *Transfusion* 33:30 (1993).

There is thus a need for compositions and methods for treating blood, blood-derived products, and other biological materials, which will inactivate pathogens present in the products or materials without rendering the products or materials unsuitable for their intended use. Compositions which do not need to be removed from the biological material prior to its use would be particularly useful, as equipment and supplies needed to remove the compositions would be obviated and the costs of handling the biological material would be reduced. This places an additional requirement on the composition, however, in that if the composition remains in the biological material, it must not pose a hazard when the biological material is used for its intended purpose. For example, a highly toxic compound which inactivates pathogens in a blood sample would preclude the use of that blood for transfusion purposes (although the blood sample may still be suitable for laboratory analysis).

It is one intention of this invention to provide compositions and methods of use of the compositions for inactivating pathogens in biological materials, without rendering the materials unsuitable for their intended purpose. Examples of how this may be accomplished include, but are not limited to, using the compounds in an ex vivo or in vitro treatment of the biological materials and then removing the compounds prior to the use of the material; by using a composition which, even though it remains in the material, does not render the material unsuitable for its intended use; or by using a composition which, after inactivating pathogens in the material, will break down to products, where the breakdown products can remain in the material without rendering the material unsuitable for its intended use.

DISCLOSURE OF THE INVENTION

Accordingly, it is an object of this invention to provide compounds for inactivating pathogens in a material, where such compounds comprise a nucleic acid binding moiety; an effector moiety, capable of forming a covalent bond with nucleic acid; and a frangible linker covalently linking the nucleic acid moiety and the effector moiety; wherein the frangible linker degrades so as to no longer covalently link the nucleic acid binding moiety and the effector moiety, under conditions which do not render the material unsuitable for its intended purpose.

It is an additional object of this invention to provide such compounds for inactivating pathogens in a material, wherein the nucleic acid binding moiety is selected from the group consisting of acridine, acridine derivatives, psoralen, isopsoralen and psoralen derivatives.

It is an additional object of this invention to provide such compounds for inactivating pathogens in a material, wherein the frangible linker comprises a functional unit selected from the group consisting of forward esters, reverse esters, forward amides, reverse amides, forward thioesters, reverse thioesters, forward and reverse thionoesters, forward and reverse dithioic acids, sulfates, forward and reverse sulfonates, phosphates, and forward and reverse phosphonate groups, as defined herein.

It is an additional object of this invention to provide such compounds for inactivating pathogens in a material, wherein the effector group comprises a functional unit which is an alkylating agent.

It is an additional object of this invention to provide such compounds for inactivating pathogens in a material, wherein the effector group comprises a functional unit selected from the group consisting of mustard groups, mustard group equivalents, epoxides, aldehydes, and formaldehyde synthons.

It is an additional object of this invention to provide compounds of the formula:

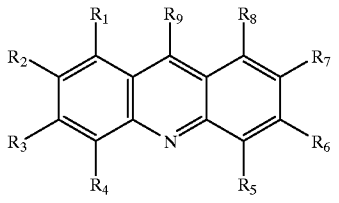

wherein at least one of $R_1$, $R_2$, $R_3$, $R_4$, $R_5$, $R_6$, $R_7$, $R_8$ and $R_9$ is -V-W-X-E as defined below, and the remainder of $R_1$, $R_2$, $R_3$, $R_4$, $R_5$, $R_6$, $R_7$, $R_8$ and $R_9$ are independently selected from the group consisting of —H, —$R_{10}$, —O—$R_{10}$, —$NO_2$, —$NH_2$, —NH—$R_{10}$, —$N(R_{10})_2$, —F, —Cl, —Br, —I, —C(=O)—$R_{10}$, —C(=O)—O—$R_{10}$, and —O—C(=O)—$R_{10}$, where —$R_{10}$ is independently H, —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, -heteroaryl-$C_{1-3}$alkyl, -heteroaryl-$C_{1-3}$ heteroalkyl, —$C_{1-3}$alkyl-aryl-$C_{1-3}$ alkyl, —$C_{1-3}$ heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

V is independently —$R_{11}$—, —NH—$R_{11}$— or —$N(CH_3)$—$R_{11}$—, where —$R_{11}$— is independently —$C_{1-8}$ alkyl-, —$C_{1-8}$heteroalkyl-, -aryl-, -heteroaryl-, —$C_{1-3}$ alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$ heteroalkyl-, -heteroaryl-$C_{1-3}$alkyl-, -heteroaryl-$C_{1-3}$ heteroalkyl-, —$C_{1-3}$alkyl-aryl-$C_{1-3}$ alkyl-, —$C_{1-3}$ heteroalkyl-aryl-$C_{1-3}$ alkyl-, —$C_{1-3}$alkyl-heteroaryl-$C_{1-3}$ alkyl-, —$C_{1-3}$alkyl-aryl-$C_{1-3}$ heteroalkyl-, —$C_{1-3}$ heteroalkyl-heteroaryl-$C_{1-3}$ alkyl-, —$C_{1-3}$heteroalkyl-aryl-$C_{1-3}$ heteroalkyl-, —$C_{1-3}$alkyl-heteroaryl-$C_{1-3}$ heteroalkyl-, or —$C_{1-3}$heteroalkyl-heteroaryl-$C_{1-3}$ heteroalkyl-;

W is independently —C(=O)—O—, —O—C—(=O)—, —C(=S)—O—, —O—C(=S)—, —C(=S)—S—, —S—C(=S)—, —C(=O)—S—, —S—C(=O)—, —O—$S(=O)_2$—O—, —$S(=O)_2$—O—, —O—$S(=O)_2$—, —C(=O)—$NR_{10}$—, —$NR_{10}$—C(=O)—, —O—P(=O)(—$OR_{10}$)—O—, —P(=O)(—$OR_{10}$)—O—, —O—P(=O)(—$OR_{10}$)—;

X is independently —$R_{11}$—; and

E is independently selected from the group consisting of —$N(R_{12})_2$, —$N(R_{12})(R_{13})$, —S—$R_{12}$, and

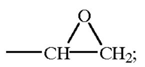

where —$R_{12}$ is —$CH_2CH_2$-G, where each G is independently —Cl, —Br, —I, —O—$S(=0)_2$—$CH_3$, —O—$S(=O)_2$—$CH_2$—$C_6H_5$, or —O—$S(=0)_2$—$C_6H_4$—$CH_3$;

and where $R_{13}$ is independently —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, -heteroaryl-$C_{1-3}$alkyl, -heteroaryl-$C_{1-3}$ heteroalkyl, —$C_{1-3}$alkyl-aryl-$C_{1-3}$ alkyl, —$C_{1-3}$ heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$heteroalkyl;

and all salts and stereoisomers (including enantiomers and diastereomers) thereof.

It is another object of this invention to provide compounds of the formula:

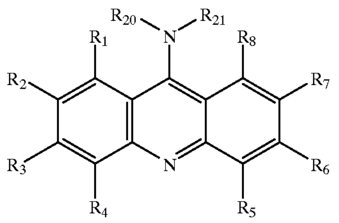

where $R_1$, $R_2$, $R_3$, $R_4$, $R_5$, $R_6$, $R_7$, and $R_8$ are independently selected from the group consisting of —H, —$R_{10}$, —O—$R_{10}$, —$NO_2$, —$NH_2$, —NH—$R_{10}$, —$N(R_{10})_2$, —F, —Cl, —Br, —I, —C(=O)—$R_{10}$, —C(=O)—O—$R_{10}$, and —O—C(=O)—$R_{10}$, where —$R_{10}$ is independently H, —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, -heteroaryl-$C_{1-3}$alkyl, -heteroaryl-$C_{1-3}$ heteroalkyl, —$C_{1-3}$alkyl-aryl-$C_{1-3}$ alkyl, -$C_{1-3}$heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

$R_{20}$ is —H or —$CH_3$; and $R_{21}$ is —$R_{11}$-W-X-E, where —$R_{11}$— is independently —$C_{1-8}$alkyl-, —$C_{1-8}$heteroalkyl-, -aryl-, -heteroaryl-, —$C_{1-3}$alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$heteroalkyl-, -heteroaryl-$C_{1-3}$alkyl-, -heteroaryl-$C_{1-3}$heteroalkyl-, —$C_{1-3}$alkyl-aryl-$C_{,-3}$ alkyl-, —$C_{1-3}$ heteroalkyl-aryl-$C_{1-3}$ alkyl-, —$C_{1-3}$alkyl-heteroaryl-$C_{1-3}$ alkyl-, —$C_{1-3}$alkyl-aryl-$C_{1-3}$ heteroalkyl-, —$C_{1-3}$ heteroalkyl-heteroaryl-$C_{1-3}$ alkyl-, —$C_{1-3}$heteroalkyl-aryl-$C_{1-3}$ heteroalkyl-, —$C_{1-3}$alkyl-heteroaryl-$C_{1-3}$ heteroalkyl-, or —$C_{1-3}$heteroalkyl-heteroaryl-$C_{1-3}$ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—NR$_{10}$—, —NR$_{10}$—C(=O)—, —O—P(=O)(—OR$_{10}$)—O—, —P(=O)(—OR$_{10}$)—O—, —O—P(=O)(—OR$_{10}$)—;

X is independently —R$_{11}$—; and

E is independently selected from the group consisting of —N(R$_{12}$)$_2$, —N(R$_{12}$)(R$_{13}$), —S—R$_{12}$, and

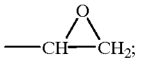

where —R$_{12}$ is —$CH_2CH_2$-G, where each G is independently —Cl, —Br, —I, —O—S(=O)$_2$—$CH_3$, —O—S(=O)$_2$—$CH_2$—$C_6H_5$, or —O—S(=O)$_2$—$C_6H_4$—$CH_3$;

and where R$_{13}$ is independently —$C_{1-8}$alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, -heteroaryl-$C_{1-3}$alkyl, -heteroaryl-$C_{1-3}$ heteroalkyl, —$C_{1-3}$alkyl-aryl-$C_{1-3}$ alkyl, —$C_{1-3}$ heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

and all salts and stereoisomers (including enantiomers and diastereomers) thereof.

It is another object of this invention to provide compounds of the formula:

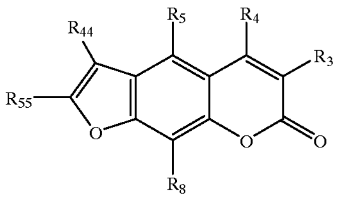

wherein at least one of R$_{44}$, R$_{55}$, R$_3$, R$_4$, R$_5$, and R$_8$ is -V-W-X-E, and the remainder of R$_{44}$, R$_{55}$, R$_3$, R$_4$, R$_5$, and R$_8$ are independently selected from the group consisting of —H, —R$_{10}$, —O—R$_{10}$, —$NO_2$, —$NH_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$, where —R$_{10}$ is independently H, —$C_{1-8}$ alkyl, —$C_{1-8}$ heteroalkyl, -aryl, -heteroaryl, —$C_{1-3}$alkyl-aryl, —$C_{1-3}$heteroalkyl-aryl, —$C_{1-3}$alkyl-heteroaryl, —$C_{1-3}$heteroalkyl-heteroaryl, -aryl-$C_{1-3}$alkyl, -aryl-$C_{1-3}$heteroalkyl, -heteroaryl-$C_{1-3}$alkyl, -heteroaryl-$C_{1-3}$heteroalkyl, —$C_{1-3}$alkyl-aryl-$C_{1-3}$ alkyl, —$C_{1-3}$heteroalkyl-aryl-$C_{1-3}$ alkyl, —$C_{1-3}$alkyl-heteroaryl-$C_{1-3}$ alkyl, —$C_{1-3}$alkyl-aryl-$C_{1-3}$ heteroalkyl, —$C_{1-3}$ heteroalkyl-heteroaryl-$C_{1-3}$ alkyl, —$C_{1-3}$heteroalkyl-aryl-$C_{1-3}$ heteroalkyl, —$C_{1-3}$alkyl-heteroaryl-$C_{1-3}$ heteroalkyl, or —$C_{1-3}$heteroalkyl-heteroaryl-$C_{1-3}$ heteroalkyl;

V is independently —R$_{11}$—, —NH—R$_{11}$— or —N($CH_3$)—R$_{11}$—, where —R$_{11}$— is independently —$C_{1-8}$ alkyl-, —$C_{1-8}$heteroalkyl-, -aryl-, -heteroaryl-, —$C_{1-3}$ alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$ heteroalkyl-, -heteroaryl-$C_{1-3}$alkyl-, -heteroaryl-$C_{1-3}$ heteroalkyl-, —$C_{1-3}$alkyl-aryl-$C_{1-3}$ alkyl-, —$C_{1-3}$ heteroalkyl-aryl-$C_{1-3}$ alkyl-, —$C_{1-3}$alkyl-heteroaryl-$C_{1-3}$ alkyl-, —$C_{1-3}$alkyl-aryl-$C_{1-3}$ heteroalkyl-, —$C_{1-3}$ heteroalkyl-heteroaryl-$C_{1-3}$ alkyl-, —$C_{1-3}$heteroalkyl-aryl-$C_{1-3}$ heteroalkyl-, —$C_{1-3}$alkyl-heteroaryl-$C_{1-3}$ heteroalkyl-, or —$C_{1-3}$heteroalkyl-heteroaryl-$C_{1-3}$ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—NR$_{10}$—, —NR$_{10}$—C(=O)—, —O—P(=O)(—OR$_{10}$)—O—, —P(=O)(—OR$_{10}$)—O—, —O—P(=O)(—OR$_{10}$)—;

X is independently —R$_{11}$—; and

E is independently selected from the group consisting of —N(R$_{12}$)$_2$, —N(R$_{12}$)(R$_{13}$), —S—R$_{12}$, and

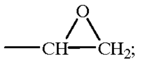

where —R$_{l2}$ is —$CH_2CH_2$-G, where each G is independently —Cl, —Br, —I, —O—S(=O)$_2$—$CH_3$, —O—S(=O)$_2$—$CH_2$—$C_6H_5$, or O—S(=O)$_2$—$C_6H_4$—$CH_3$;

and where R$_{13}$ is independently —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, heteroaryl-$C_{1-3}$alkyl-, heteroaryl-$C_{1-3}$ heteroalkyl, —$C_{1-3}$alkyl-aryl-$C_{1-3}$ alkyl, —$C_{1-3}$ heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

and all salts and stereoisomers (including enantiomers and diastereomers) thereof.

It is yet another object of this invention to provide the compounds β-alanine, N(2-carbomethoxyacridin-9-yl), 2-[bis(2-chloroethyl)amino]ethyl ester; 4-aminobutyric acid N-[(2-carbomethoxyacridin-9-yl), 2-[bis(2-chloroethyl) amino]ethyl ester; 5-aminovaleric acid N-[(2-carbomethoxyacridin-9-yl), 2-[bis(2-chloroethyl)amino] ethyl ester; β-alanine, N-(2-carbomethoxyacridin-9yl), 3-[bis(2-chloroethyl)amino]propyl ester; β-alanine, [,N-bis (2-chloroethyl)], 3-[(6-chloro-2-methoxyacridin-9-yl) amino]propyl ester; β-alanine, [N,N-bis(2-chloroethyl)], 2-[(6-chloro-2-methoxyacridin-9-yl)amino]ethyl ester; [N,N-bis(2-chloroethyl)]-2-aminoethyl 4,5',8-trimethyl-4'-psoralenacetate; and alanine, N-(acridin-9-yl), 2-[bis(2-chloroethyl)amino]ethyl ester; and all salts thereof.

Provided are methods for inactivating pathogens in a material, such as a biological material, the methods comprising adding one or more compounds of the invention to the material; and incubating the material. The compound may be added to the material to form a final solution having a concentration of the compound (or total concentration of all compounds, if more than one is used), for example, of between 1 and 500 μM. Biological materials which may be treated include blood, blood products, plasma, platelet preparations, red blood cells, packed red blood cells, serum, cerebrospinal fluid, saliva, urine, sweat, feces, semen, milk, tissue samples, and homogenized tissue samples, derived from human or other mammalian or vertebrate sources.

BEST MODE FOR CARRYING OUT THE INVENTION

This invention provides for compounds useful for inactivating pathogens found in materials, particularly for inactivating pathogens found in biological materials such as blood or other body fluids. This invention also provides for methods of use of such compounds for inactivating pathogens in materials. The invention also provides for inactivating pathogens found in or on materials for biological use. The compounds may be used in vitro and ex vivo. The biological materials or materials for biological use may be intended for use in vitro, in vivo, or ex vivo.

The compounds are designed to inactivate pathogens by reacting with nucleic acid. In aqueous solution, at appropriate pH values, the compounds have a period of activity during which they can bind to and react with nucleic acid. After this period, the compounds break down to products which are no longer able to bind to nor react with nucleic acid.

The chemical organization of the compounds can be broadly described as an anchor, covalently bonded to a frangible linker, which is covalently bonded to an effector. "Anchor" is defined as a moiety which binds non-covalently to a nucleic acid biopolymer (DNA or RNA). "Effector" is defined as a moiety which reacts with nucleic acid by a mechanism which forms a covalent bond with the nucleic acid. "Frangible linker" is defined as a moiety which serves to covalently link the anchor and effector, and which will degrade under certain conditions so that the anchor and effector are no longer linked covalently. The anchor-frangible linker-effector arrangement enables the compounds to bind specifically to nucleic acid (due to the anchor's binding ability). This brings the effector into proximity for reaction with the nucleic acid.

The compounds are useful for inactivating pathogens found in materials, particularly biological materials such as blood and other body fluids. Intracellular and extracellular and or other pathogen materials may be inactivated. For example, when a compound of the invention is combined with a pathogen-containing red blood cell composition at physiological pH, the effector portion of the compound reacts with pathogen nucleic acid. Effector moieties which do not react with nucleic acid are gradually hydrolyzed by the solvent. Hydrolysis of the frangible linker occurs concurrently with the effector-nucleic acid reaction and effector hydrolysis. It is desirable that the frangible linker break down at a rate slow enough to permit inactivation of pathogens in the material; that is, the rate of breakdown of the frangible linker is slower than the rate at which the compound reacts with nucleic acid. After a sufficient amount of time has passed, the compound has broken down into the anchor (which may also bear fragments of the frangible linker) and the effector-nucleic acid breakdown products (where fragments of the frangible linker may also remain attached to the effector), or into the anchor (which may also bear fragments of the frangible linker) and the hydrolyzed effector breakdown products (where fragments of the frangible linker may also remain attached to the effector). Additional fragments of the frangible linker may also be generated upon degradation of the compound which do not remain bonded to either the anchor or the effector. The exact embodiment of the compound of the invention determines whether the anchor breakdown product or the effector breakdown product bears fragments of the frangible linker, or whether additional fragments of the frangible linker are generated which do not remain bonded to either the anchor or the effector breakdown products.

A preferred embodiment of the invention comprises compounds which, upon cleavage of the frangible linker, result in breakdown products of low mutagenicity. Mutagenicity of the compounds, after hydrolysis of the effector, is due primarily to the anchor moiety, as the anchor interacts with nucleic acid and may have the potential to interfere with nucleic acid replication, even if the effector moiety has been hydrolyzed. Preferably, after cleavage of the frangible linker, the anchor fragment has substantially reduced mutagenicity.

Definitions

"Pathogen" is defined as any nucleic acid containing agent capable of causing disease in a human, other mammals, or vertebrates. Examples include microorganisms such as unicellular or multicellular microorganisms. Examples of pathogens are bacteria, viruses, protozoa, fungi, yeasts, molds, and mycoplasmas which cause disease in humans, other mammals, or vertebrates. The genetic material of the pathogen may be DNA or RNA, and the genetic material may be present as single-stranded or double-stranded nucleic acid. The nucleic acid of the pathogen may be in solution, intracellular, extracellular, or bound to cells. Table I lists examples of viruses, and is not intended to limit the invention in any manner.

TABLE I

| Family: | Virus: |
|---|---|
| Adeno | Adenovirus 2 |
| | Canine hepatitis |
| Arena | Pichinde |
| | Lassa |
| Bunya | Turlock |
| | California encephalitis |
| Herpes | Herpes simplex 1 |
| | Herpes simplex 2 |
| | Cytomegalovirus |
| | Pseudorabies |
| Orothomyxo | Influenza |
| Papova | SV-40 |
| Paramyxo | Measles |
| | Mumps |
| | Parainfluenza 2 and 3 |
| Picorna | Poliovirus 1 and 2 |
| | Coxsackie A-9 |
| | Echo 11 |
| Pox | Vaccinia |
| | Fowl Pox |
| Reo | |
| | Blue tongue |
| | Colorado tick fever |
| Retro | HIV |
| | Avian sarcoma |
| | Murine sarcoma |
| | Murine leukemia |
| Rhabdo | Vesicular stomatitis virus |
| Toga | Western equine encephalitis |
| | Dengue 2 |
| | Dengue 4 |
| | St. Louis encephalitis |
| Hepadna | hepatitis B |

TABLE I-continued

| Family: | Virus: |
| --- | --- |
| Bacteriophage | Lambda |
| | T2 |
| (Rickettsia) | *R. akari* (rickettsialpox) |

"In vivo" use of a material or compound is defined as introduction of the material or compound into a living human, mammal, or vertebrate.

"In vitro" use of a material or compound is defined as a use of the material or compound outside a living human, mammal, or vertebrate, where neither the material nor compound is intended for reintroduction into a living human, mammal, or vertebrate. An example of an in vitro use would be the analysis of components of a blood sample using laboratory equipment.

"Ex vivo" use of a compound is defined as using a compound for treatment of a biological material outside a living human, mammal, or vertebrate, where that treated biological material is intended for use inside a living human, mammal, or vertebrate. For example, removal of blood from a human, and introduction of a compound into that blood to inactivate pathogens, is defined as an ex vivo use of that compound if the blood is intended for reintroduction into that human or another human. Reintroduction of the human blood into that human or another human would be in vivo use of the blood, as opposed to the ex vivo use of the compound. If the compound is still present in the blood when it is reintroduced into the human, then the compound, in addition to its ex vivo use, is also introduced in vivo.

"Biological material" is defined as a material originating from a biological organism of any type. Examples of biological materials include, but are not limited to, blood, blood products such as plasma, platelet preparations, red blood cells, packed red blood cells, and serum, cerebrospinal fluid, saliva, urine, feces, semen, sweat, milk, tissue samples, homogenized tissue samples, and any other substance having its origin in a biological organism. Biological materials also include synthetic material incorporating a substance having its origin in a biological organism, such as a vaccine preparation comprised of alum and a pathogen (the pathogen, in this case, being the substance having its origin in a biological organism), a sample prepared for analysis which is a mixture of blood and analytical reagents, cell culture medium, cell cultures, viral cultures, and other cultures derived from a living organism.

"Material for biological use" is defined as any material that will come into contact with, or be introduced into, a living human, mammal, or vertebrate, where such contact carries a risk of transmitting disease or pathogens. Such materials include, but are not limited to, medical implants such as pacemakers and artificial joints; implants designed for sustained drug release; needles, intravenous lines, and the like; dental tools; dental materials such as tooth crowns; catheters; and any other material which, when in contact with or introduced into a living human, mammal, or vertebrate, entails risk of transmitting disease or pathogens.

"Inactivation of pathogens" is defined as rendering pathogens in a material incapable of reproducing. Inactivation is expressed as the negative logarithm of the fraction of remaining pathogens capable of reproducing. Thus, if a compound at a certain concentration renders 99% of the pathogens in a material incapable of reproduction, 1% or one-one hundredth (0.01) of the pathogens remain capable of reproduction. The negative logarithm of 0.01 is 2, and that concentration of that compound is said to have inactivated the pathogens present by 2 logs. Alternatively, the compound is said to have 2 logs kill at that concentration.

"Alkyl" as used herein refers to a cyclic, branched, or straight chain chemical group containing carbon and hydrogen, such as methyl, pentyl, and adamantyl. Alkyl groups can either be unsubstituted or substituted with one or more substituents, e.g., halogen, alkoxy, acyloxy, amino, hydroxyl, thiol, carboxy, benzyloxy, phenyl, benzyl, or other functionality. Alkyl groups can be saturated or unsaturated (e.g., containing —C═C— or —C—C— subunits), at one or several positions. Typically, alkyl groups will comprise 1 to 12 carbon atoms, preferably 1 to 10 carbon atoms, and more preferably 1 to 8 carbon atoms, unless otherwise specified.

"Heteroalkyl" as used herein are alkyl chains with one or more N, O, S, or P heteroatoms incorporated into the chain. The heteroatom(s) may bear none, one, or more than one of the substituents described above. "Heteroatoms" also includes oxidized forms of the heteroatoms N, S and P. Examples of heteroalkyl groups include (but are not limited to) methoxy, ethoxy, and other alkyloxy groups; ether-containing groups; amide containing groups such as polypeptide chains; ring systems such as piperidinyl, lactam and lactone; and other groups which incorporate heteroatoms into the carbon chain. Typically, heteroalkyl groups will comprise, in addition to the heteroatom(s), 1 to 12 carbon atoms, preferably 1 to 10 carbon atoms, and more preferably 1 to 8 carbon atoms, unless otherwise specified.

"Aryl" or "Ar" refers to an unsaturated aromatic carbocyclic group having a single ring (e.g., phenyl) or multiple condensed rings (e.g., naphthyl or anthryl), which can be optionally unsubstituted or substituted with amino, hydroxyl, $C_{1-8}$ alkyl, alkoxy, halo, thiol, and other substituents.

"Heteroaryl" groups are unsaturated aromatic carbocyclic groups having a single ring (e.g., pyridyl or furyl) or multiple condensed rings (e.g., acridinyl, indolyl or benzothienyl) and having at least one hetero atom, such as N, O, or S, within at least one of the rings. The ring(s) can optionally be unsubstituted or substituted with amino, hydroxyl, alkyl, alkoxy, halo, thiol, acyloxy, carboxy, benzyloxy, phenyl, benzyl, and other substituents.

Abbreviations

The following abbreviations are used: QM (quinacrine mustard); Hct (hematocrit); RBC (red blood cell); LB (Luria Broth); cfu (colony forming units); pfu (plaque forming units); DMEM (Delbecco's modified eagles medium); FBS (fetal bovine serum); PRBC (packed red blood cells); rpm (revolutions per minute); TC (tissue culture); NHSP (normal human serum pool); NCS (newborn calf serum); PBS (phosphate buffered saline).

Chemical Structure of the Compounds

A wide variety of groups are available for use as the anchors, linkers, and effectors. Examples of anchor groups which can be used in the compound include, but are not limited to, intercalators, minor groove binders, major groove binders, molecules which bind by electrostatic interactions such as polyamines, and molecules which bind by sequence specific interactions. The following is a non-limiting list of possible anchor groups:

acridines (and acridine derivatives, e.g. proflavine, acriflavine, diacridines, acridones, benzacridines, quinacrines), actinomycins, anthracyclinones, rhodomycins, daunomycin, thioxanthenones (and thioxanthenone derivatives, e.g. miracil D), anthramycin, mitomycins, echinomycin (quinomycin A), triostins, ellipticine (and dimers, trimers and analogs thereof), norphilin A, fluorenes (and derivatives, e.g. flourenones, fluorenodiamines), phenazines, phenanthridines, phenothiazines (e.g., chlorpromazine), phenoxazines, benzothiazoles, xanthenes and thioxanthenes, anthraquinones, anthrapyrazoles, benzothiopyranoindoles, 3,4-benzopyrene, 1-pyrenyloxirane, benzanthracenes, benzodipyrones, quinolines (e.g., chloroquine, quinine, phenylquinoline carboxamides), furocoumarins (e.g., psoralens and isopsoralens), ethidium, propidium, coralyne, and polycyclic aromatic hydrocarbons and their oxirane derivatives;

distamycin, netropsin, other lexitropsins, Hoechst 33258 and other Hoechst dyes, DAPI (4',6-diamidino-2-phenylindole), berenil, and triarylmethane dyes;

aflatoxins;

spermine, spermidine, and other polyamines; and nucleic acids or analogs which bind by sequence specific interactions such as triple helix formation, D-loop formation, and direct base pairing to single stranded targets. Derivatives of these compounds are also non-limiting examples of anchor groups, where a derivative of a compound includes, but is not limited to, a compound which bears one or more substituent of any type at any location, oxidation or reduction products of the compound, etc.

Examples of linkers which can be used in the invention are, but are not limited to, compounds which include functional groups such as ester (where the carbonyl carbon of the ester is between the anchor and the $sp^3$ oxygen of the ester; this arrangement is also called "forward ester"), "reverse ester" (where the $sp^3$ oxygen of the ester is between the anchor and the carbonyl carbon of the ester), thioester (where the carbonyl carbon of the thioester is between the anchor and the sulfur of the thioester, also called "forward thioester"), reverse thioester (where the sulfur of the thioester is between the anchor and the carbonyl carbon of the thioester, also called "reverse thioester"), forward and reverse thionoester, forward and reverse dithioic acid, sulfate, forward and reverse sulfonates, phosphate, and forward and reverse phosphonate groups. "Thioester" designates the —C(=O)—S— group; "thionoester" designates the —C(=S)—O— group, and "dithioic acid" designates the —C(=S)—S— group. The frangible linker also may include an amide, where the carbonyl carbon of the amide is between the anchor and the nitrogen of the amide (also called a "forward amide"), or where the nitrogen of the amide is between the anchor and the carbonyl carbon of the amide (also called a "reverse amide"). For groups which can be designated as "forward" and "reverse", the forward orientation is that orientation of the functional groups wherein, after hydrolysis of the functional group, the resulting acidic function is covalently linked to the anchor moiety and the resulting alcohol or thiol function is covalently linked to the effector moiety. The reverse orientation is that orientation of the functional groups wherein, after hydrolysis of the functional group, the resulting acidic function is covalently linked to the effector moiety and the resulting alcohol or thiol function is covalently linked to the anchor moiety.

The frangible linker, such as an amide moiety, also may be capable of degrading under conditions of enzymatic degradation, by endogenous enzymes in the biological material being treated, or by enzymes added to the material.

Examples of effectors which can be used in the invention are, but are not limited to, mustard groups, mustard group equivalents, epoxides, aldehydes, formaldehyde synthons, and other alkylating and cross-linking agents. Mustard groups are defined as including mono or bis haloethylamine groups, and mono haloethylsulfide groups. Mustard group equivalents are defined by groups that react by a mechanism similar to the mustards (that is, by forming an aziridinium intermediate, or by having or by forming an aziridine ring, which can react with a nucleophile), such as mono or bis mesylethylamine groups, mono mesylethylsulfide groups, mono or bis tosylethylamine groups, and mono tosylethylsulfide groups. Formaldehyde synthons are defined as any compound that breaks down to formaldehyde in aqueous solution, including hydroxymethylamines such as hydroxymethylglycine. Examples of formaldehyde synthons are given in U.S. Pat. No. 4,337,269 and in International Patent Application WO 97/02028. While the invention is not limited to any specific mechanism, the effector groups, which are, or are capable of forming an electrophilic group, such as a mustard group, are believed to react with and form a covalent bond to nucleic acid.

Three embodiments of the compounds of this invention are described by the following general formulas I, II, and III.

General formula I is:

(I)

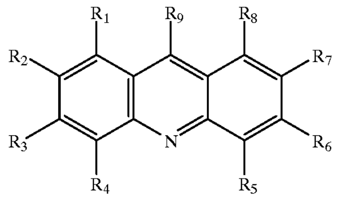

wherein at least one of $R_1$, $R_2$, $R_3$, $R_4$, $R_5$, $R_6$, $R_7$, $R_8$ and $R_9$ is -V-W-X-E as defined below, and the remainder of $R_1$, $R_2$, $R_3$, $R_4$, $R_5$, $R_6$, $R_7$, $R_8$ and $R_9$ are independently selected from the group consisting of —H, —$R_{10}$, —O—$R_{10}$, —$NO_2$, —$NH_2$, —NH—$R_{10}$, —$N(R_{10})_2$, —F, —Cl, —Br, —I, —C(=O)—$R_{10}$, —C(=O)—O—$R_{10}$, and —O—C(=O)—$R_{10}$, where —$R_{10}$ is independently H, —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, -heteroaryl-$C_{1-3}$alkyl, -heteroaryl-$C_{1-3}$ heteroalkyl, —$C_{1-3}$alkyl-aryl-$C_{1-3}$ alkyl, —$C_{1-3}$ heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

V is independently —$R_{11}$—, —NH—$R_{11}$— or —$N(CH_3)$—$R_{11}$—, where —$R_{11}$— is independently —$C_{1-8}$ alkyl-, —$C_{1-8}$heteroalkyl-, -aryl-, -heteroaryl-, —$C_{1-3}$ alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$ heteroalkyl-, -heteroaryl-$C_{1-3}$alkyl-, -heteroaryl-$C_{1-3}$ heteroalkyl-, —$C_{1-3}$alkyl-aryl-$C_{1-3}$ alkyl-, —$C_{1-3}$ heteroalkyl-aryl-$C_{1-3}$ alkyl-, —$C_{1-3}$alkyl-heteroaryl-$C_{1-3}$ alkyl-, —$C_{1-3}$alkyl-aryl-$C_{1-3}$ heteroalkyl-, —$C_{1-3}$ heteroalkyl-heteroaryl-$C_{1-3}$ alkyl-, —$C_{1-3}$heteroalkyl-aryl-$C_{1-3}$ heteroalkyl-, —$C_{1-3}$alkyl-heteroaryl-$C_{1-3}$ heteroalkyl-, or —$C_{1-3}$heteroalkyl-heteroaryl-$C_{1-3}$ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—NR$_{10}$—, —NR$_{10}$—C(=O)—, —O—P(=O)(—OR$_{10}$)—O—, —P(=O)(—OR$_{10}$)—O—, —O—P(=O)(—OR$_{10}$)—;

X is independently —R$_{11}$—; and

E is independently selected from the group consisting of —N(R$_{12}$)$_2$, —N(R$_{12}$)(R$_{13}$), —S—R$_{12}$, and

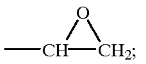

where —R$_{12}$ is —CH$_2$CH$_2$-G, where each G is independently —Cl, —Br, —I, —O—S(=O)$_2$—CH$_3$, —O—S(=O)$_2$—CH$_2$—C$_6$H$_5$, or —O—S(=O)$_2$—C$_6$H$_4$—CH$_3$;

and where R$_{13}$ is independently —C$_{1-8}$ alkyl, —C$_{1-8}$ heteroalkyl, -aryl, -heteroaryl, —C$_{1-3}$alkyl-aryl, —C$_{1-3}$ heteroalkyl-aryl, —C$_{1-3}$alkyl-heteroaryl, —C$_{1-3}$ heteroalkyl-heteroaryl, -aryl-C$_{1-3}$alkyl, -aryl-C$_{1-3}$ eteroalkyl, -heteroaryl-C$_{1-3}$alkyl, -heteroaryl-C$_{1-3}$ heteroalkyl, —C$_{1-3}$alkyl-aryl-C$_{1-3}$ alkyl, —C$_{1-3}$ heteroalkyl-aryl-C$_{1-3}$ alkyl, —C$_{1-3}$alkyl-heteroaryl-C$_{1-3}$ alkyl, —C$_{1-3}$ alkyl-aryl-C$_{1-3}$ heteroalkyl, —C$_{1-3}$heteroalkyl-heteroaryl-C$_{1-3}$ alkyl, —C$_{1-3}$heteroalkyl-aryl-C$_{1-3}$ heteroalkyl, —C$_{1-3}$ alkyl-heteroaryl-C$_{1-3}$ heteroalkyl, or —C$_{1-3}$heteroalkyl-heteroaryl-C$_{1-3}$ heteroalkyl;

and all salts and stereoisomers (including enantiomers and diastereomers) thereof.

General formula II is:

(II)

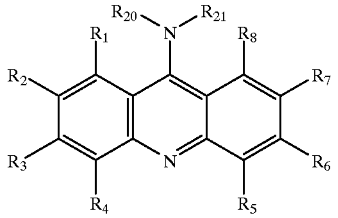

where R$_1$, R$_2$, R$_3$, R$_4$, R$_5$, R$_6$, R$_7$, and R$_8$ are independently selected from the group consisting of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$, where —R$_{10}$ is independently H, —C$_{1-8}$ alkyl, —C$_{1-8}$ heteroalkyl, -aryl, -heteroaryl, —C$_{1-3}$alkyl-aryl, —C$_{1-3}$ heteroalkyl-aryl, —C$_{1-3}$alkyl-heteroaryl, —C$_{1-3}$ heteroalkyl-heteroaryl, -aryl-C$_{1-3}$alkyl, -aryl-C$_{1-3}$ heteroalkyl, -heteroaryl-C$_{1-3}$alkyl, -heteroaryl-C$_{1-3}$ heteroalkyl, —C$_{1-3}$alkyl-aryl-C$_{1-3}$ alkyl, —C$_{1-3}$ heteroalkyl-aryl-C$_{1-3}$ alkyl, —C$_{1-3}$alkyl-heteroaryl-C$_{1-3}$ alkyl, —C$_{1-3}$ alkyl-aryl-C$_{1-3}$ heteroalkyl, —C$_{1-3}$heteroalkyl-heteroaryl-C$_{1-3}$ alkyl, —C$_{1-3}$heteroalkyl-aryl-C$_{1-3}$ heteroalkyl, —C$_{1-3}$ alkyl-heteroaryl-C$_{1-3}$ heteroalkyl, or —C$_{1-3}$heteroalkyl-heteroaryl-C$_{1-3}$ heteroalkyl;

R$_{20}$ is —H or —CH$_3$; and

R$_{21}$ is —R$_{11}$-W-X-E, where —R$_{11}$— is independently —C$_{1-8}$alkyl-, —C$_{1-8}$ heteroalkyl-, -aryl-, -heteroaryl-, —C$_{1-3}$alkyl-aryl-, —C$_{1-3}$ heteroalkyl-aryl-, —C$_{1-3}$alkyl-heteroaryl-, —C$_{1-3}$ heteroalkyl-heteroaryl-, -aryl-C$_{1-3}$alkyl-, -aryl-C$_{1-3}$ heteroalkyl-, -heteroaryl-C$_{1-3}$alkyl-, -heteroaryl-C$_{1-3}$ heteroalkyl-, —C$_{1-3}$alkyl-aryl-C$_{1-3}$ alkyl-, —C$_{1-3}$ heteroalkyl-aryl-C$_{1-3}$ alkyl-, —C$_{1-3}$alkyl-heteroaryl-C$_{1-3}$ alkyl-, —C$_{1-3}$alkyl-aryl-C$_{1-3}$ heteroalkyl-, —C$_{1-3}$ heteroalkyl-heteroaryl-C$_{1-3}$ alkyl-, —C$_{1-3}$heteroalkyl-aryl-C$_{1-3}$ heteroalkyl-, —C$_{1-3}$alkyl-heteroaryl-C$_{1-3}$ heteroalkyl-, or —C$_{1-3}$heteroalkyl-heteroaryl-C$_{1-3}$ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—NR$_{10}$—, —NR$_{10}$—C(=O)—, —O—P(=O)(—OR$_{10}$)—O—, —P(=O)(—OR$_{10}$)—O—, —O—P(=O)(—OR$_{10}$)—;

X is independently —R$_{11}$—; and

E is independently selected from the group consisting of —N(R$_{12}$)$_2$, —N(R$_{12}$)(R$_{13}$), —S—R$_{12}$, and

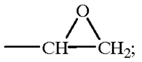

where —R$_{12}$ is —CH$_2$CH$_2$-G, where each G is independently —Cl, —Br, —I, —O—S(=O)$_2$—CH$_3$, —O—S(=O)$_2$—CH$_2$—C$_6$H$_5$, or —O—S(=O)$_2$—C$_6$H$_4$—CH$_3$;

and where R$_{13}$ is independently —C$_{1-8}$ alkyl, —C$_{1-8}$ heteroalkyl, -aryl, -heteroaryl, —C$_{1-3}$alkyl-aryl, —C$_{1-3}$ heteroalkyl-aryl, —C$_{1-3}$alkyl-heteroaryl, —C$_{1-3}$ heteroalkyl-heteroaryl, -aryl-C$_{1-3}$alkyl, -aryl-C$_{1-3}$ heteroalkyl, -heteroaryl-C$_{1-3}$alkyl, -heteroaryl-C$_{1-3}$ heteroalkyl, —C$_{1-3}$alkyl-aryl-C$_{1-3}$ alkyl, —C$_{1-3}$ eteroalkyl-aryl-C$_{1-3}$ alkyl, —C$_{1-3}$alkyl-heteroaryl-C$_{1-3}$ alkyl, —C$_{1-3}$ alkyl-aryl-C$_{1-3}$ heteroalkyl, —C$_{1-3}$heteroalkyl-heteroaryl-C$_{1-3}$ alkyl, —C$_{1-3}$heteroalkyl-aryl-C$_{1-3}$ heteroalkyl, —C$_{1-3}$ alkyl-heteroaryl-C$_{1-3}$ heteroalkyl, or —C$_{1-3}$heteroalkyl-heteroaryl-C$_{1-3}$ heteroalkyl;

and all salts and stereoisomers (including enantiomers and diastereomers) thereof General formula III is:

(III)

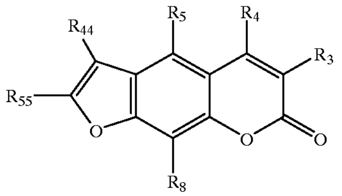

wherein at least one of R$_{44}$, R$_{55}$, R$_3$, R$_4$, R$_5$, and R$_8$ is -V-W-X-E, and the remainder of R$_{44}$, R$_{55}$, R$_3$, R$_4$, R$_5$, and R$_8$ are independently selected from the group consisting of —H, —R$_{10}$, —O—R$_{10}$, —NO$_2$, —NH$_2$, —NH—R$_{10}$, —N(R$_{10}$)$_2$, —F, —Cl, —Br, —I, —C(=O)—R$_{10}$, —C(=O)—O—R$_{10}$, and —O—C(=O)—R$_{10}$, where —R$_{10}$ is independently H, —C$_{1-8}$ alkyl, —C$_{1-8}$ heteroalkyl, -aryl, -heteroaryl, —C$_{1-3}$alkyl-aryl, —C$_{1-3}$ heteroalkyl-aryl, —C$_{1-3}$alkyl-heteroaryl, —C$_{1-3}$ heteroalkyl-heteroaryl, -aryl-C$_{1-3}$alkyl, -aryl-C$_{1-3}$ heteroalkyl, -heteroaryl-C$_{1-3}$alkyl, -heteroaryl-C$_{1-3}$ heteroalkyl, —C$_{1-3}$alkyl-aryl-C$_{1-3}$ alkyl, —C$_{1-3}$ heteroalkylaryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

V is independently —$R_{11}$—, —NH—$R_{11}$— or —N($CH_3$)—$R_{11}$—, where —$R_{11}$— is independently —$C_{1-8}$ alkyl-, —$C_{1-8}$heteroalkyl-, -aryl-, -heteroaryl-, —$C_{1-3}$ alkyl-aryl-, —$C_{1-3}$heteroalkyl-aryl-, —$C_{1-3}$alkyl-heteroaryl-, —$C_{1-3}$heteroalkyl-heteroaryl-, -aryl-$C_{1-3}$alkyl-, -aryl-$C_{1-3}$ heteroalkyl-, -heteroaryl-$C_{1-3}$alkyl-, -heteroaryl-$C_{1-3}$ heteroalkyl-, —$C_{1-3}$alkyl-aryl-$C_{1-3}$ alkyl-, —$C_{1-3}$ heteroalkyl-aryl-$C_{1-3}$ alkyl-, —$C_{1-3}$alkyl-heteroaryl-$C_{1-3}$ alkyl-, —$C_{1-3}$alkyl-aryl-$C_{1-3}$ heteroalkyl-, —$C_{1-3}$ heteroalkyl-heteroaryl-$C_{1-3}$ alkyl-, —$C_{1-3}$heteroalkyl-aryl-$C_{1-3}$ heteroalkyl-, —$C_{1-3}$alkyl-heteroaryl-$C_{1-3}$ heteroalkyl-, or —$C_{1-3}$heteroalkyl-heteroaryl-$C_{1-3}$ heteroalkyl-;

W is independently —C(=O)—O—, —O—C(=O)—, —C(=S)—O—, —O—C(=S)—, —C(=S)—S—, —S—C(=S)—, —C(=O)—S—, —S—C(=O)—, —O—S(=O)$_2$—O—, —S(=O)$_2$—O—, —O—S(=O)$_2$—, —C(=O)—$NR_{10}$—, —$NR_{10}$—C(=O)—, —O—P(=O)(—$OR_{10}$)—O—, —P(=O)(—$OR_{10}$)—O—, —O—P(=O)(—$OR_{10}$)—;

X is independently —$R_{11}$—; and

E is independently selected from the group consisting of —N($R_{12}$)$_2$, —N($R_{12}$)($R_{13}$), —S—$R_{12}$, and

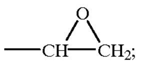

where —$R_{12}$ is —$CH_2CH_2$-G, where each G is independently —Cl, —Br, —I, —O—S(=O)$_2$—$CH_3$, —O—S(=O)$_2$—$CH_2$—$C_6H_5$, or —O—S(=O)$_2$—$C_6H_4$—$CH_3$;

and where $R_{13}$ is independently —$C_{1-8}$ alkyl, —$C_{1-8}$ heteroalkyl, -aryl, -heteroaryl, —$C_{1-3}$alkyl-aryl, —$C_{1-3}$ heteroalkyl-aryl, —$C_{1-3}$alkyl-heteroaryl, —$C_{1-3}$ heteroalkyl-heteroaryl, -aryl-$C_{1-3}$alkyl, -aryl-$C_{1-3}$ heteroalkyl, -heteroaryl-$C_{1-3}$alkyl, -heteroaryl-$C_{1-3}$ heteroalkyl, —$C_{1-3}$alkyl-aryl-$C_{1-3}$ alkyl, —$C_{1-3}$ heteroalkyl-aryl-$C_{1-3}$ alkyl, —$C_{1-3}$alkyl-heteroaryl-$C_{1-3}$ alkyl, —$C_{1-3}$ alkyl-aryl-$C_{1-3}$ heteroalkyl, —$C_{1-3}$heteroalkyl-heteroaryl-$C_{1-3}$ alkyl, —$C_{1-3}$heteroalkyl-aryl-$C_{1-3}$ heteroalkyl, —$C_{1-3}$ alkyl-heteroaryl-$C_{1-3}$ heteroalkyl, or —$C_{1-3}$heteroalkyl-heteroaryl-$C_{1-3}$ heteroalkyl;

and all salts and stereoisomers (including enantiomers and diastereomers) thereof.

It will be appreciated that, in general formula I above, the acridine nucleus is the anchor moiety, the -V-W-X- group(s) comprises the frangible linker, and the E group(s) is the effector group. Similarly, in general formula III above, the psoralen nucleus is the anchor moiety, the -V-W-X- group(s) comprises the frangible linker, and the E group(s) is the effector group. General formula II is a subset of general formula I.

An exemplary compound of the invention is the structure below, designated IV:

IV

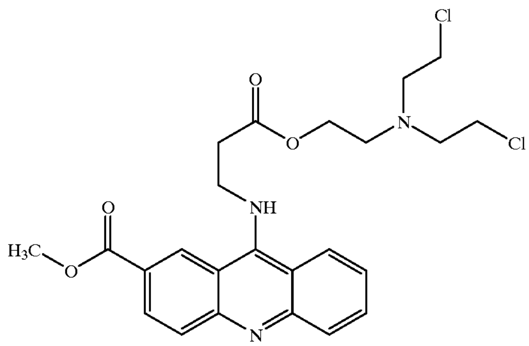

In IV, a 2-carbomethoxyacridine ring system serves as the anchor moiety via intercalation. A bis (chloroethyl) amine group serves as the effector moiety, which can alkylate nucleic acid; the nitrogen mustard hydrolyzes if it does not react with nucleic acid. The linker is —NH—$CH_2CH_2$—C(=O)—O—$CH_2CH_2$—. In aqueous solution at physiological pH, this ester-containing linker hydrolyzes within hours. Changing the pH of the solution changes the rate at which the linker hydrolyzes; for the corresponding alcohol analog of IV (where the —Cl atoms of IV are replaced with —OH groups), $\leqq$1% hydrolysis of the ester linkage is observed at pH 3 after 100 minutes at 37° C.; at pH 8, more than 50% hydrolysis of the ester linkage is observed after 100 minutes at 37° C. The resulting hydrolysis products of IV are N-(2-carbomethoxy-9-acridinyl)-β-alanine and triethanolamine:

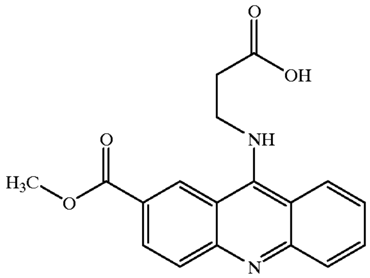

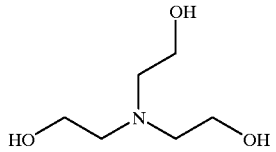

where the 2-carbomethoxyacridine bears β-alanine as a linker fragment, and the effector breakdown product bears an ethanol group as a linker fragment.

At physiological pH values, the carboxylate of the β-alanine will be negatively charged, a feature which decreases the tendency of the attached 2-carbomethoxyacridine group to intercalate into a negatively charged nucleic acid molecule. This lowers the mutagenicity of N-(2-carbomethoxy-9-acridinyl)-β-alanine relative to 9-aminoacridine. This potential for lowering the mutagenicity of the anchor fragment illustrates one advantage provided by the frangible linker.

Another advantage of the frangible linker in compounds similar to IV is that the hydrolysis rate can be adjusted by varying the length of the linker arm between the 9-aminoacridine anchor moiety and the ester function. As described in Example 7 and Tables III and IV below, an increase in the number of methylene groups between the aminoacridine anchor and the ester group results in a decrease in the amount of hydrolysis seen in aqueous solution, at pH 8, 37° C., for diol analogs of certain compounds of the invention (where the —Cl atoms of the mustards are replaced with —OH groups).

Examples of the compounds of the invention are given below, as illustration and not as any limitation on the invention.

IV

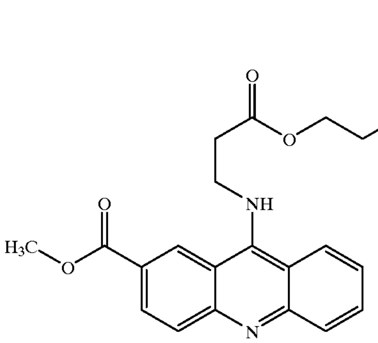

VI

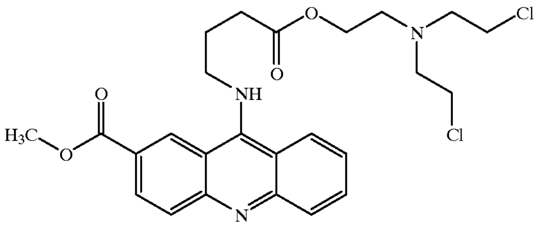

XI

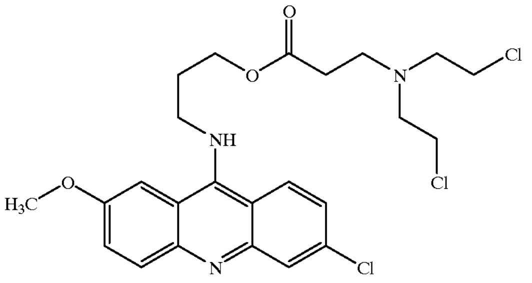

VII

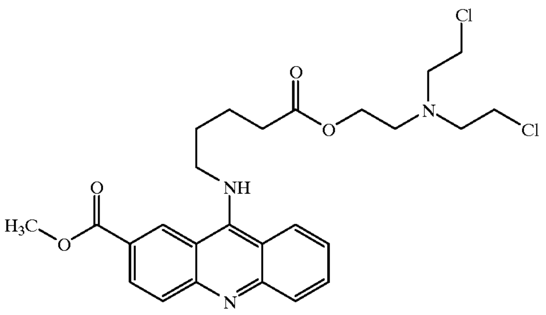

-continued

XII

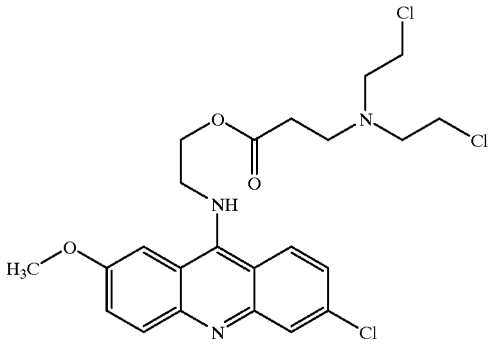

VIII

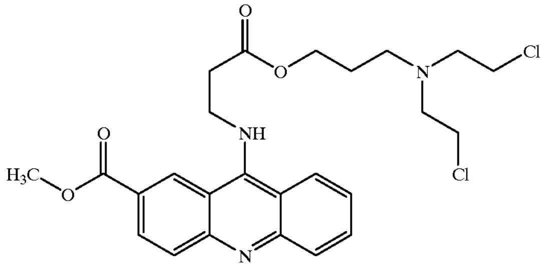

V

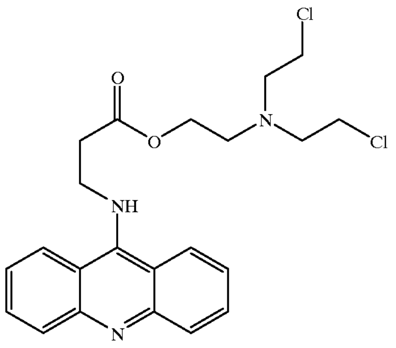

IX

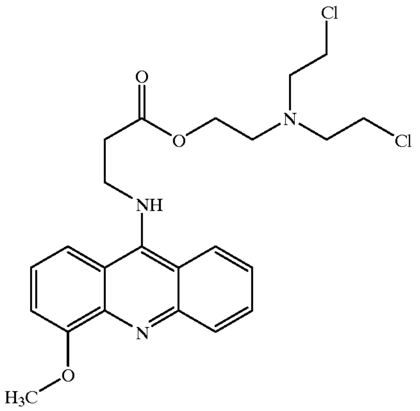

-continued

X

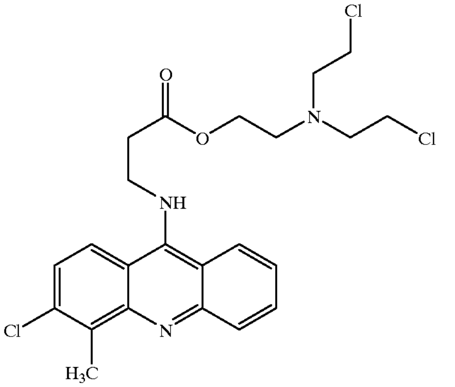

XIII

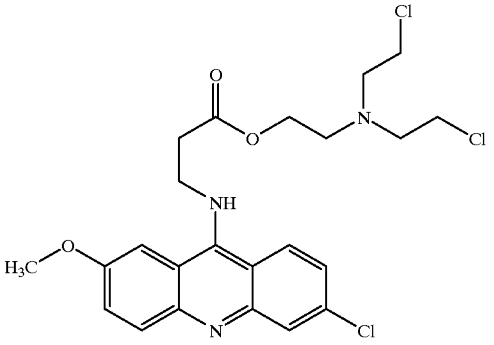

XIV

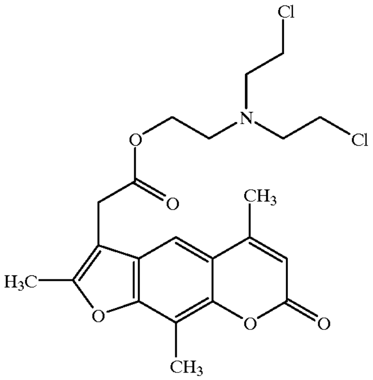

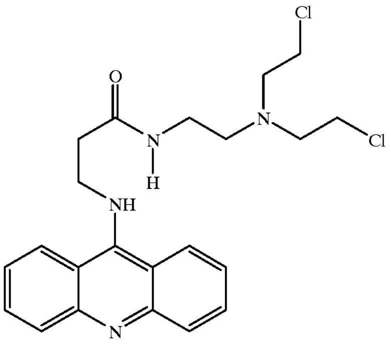

Applications

Examples of uses of the compounds of the invention include, but are not limited to: addition of the compounds of the invention in solid or solution form to biological materials, to inactivate pathogens present in the biological materials; immersion or other treatment of a material for biological use in a solution of the compounds of the invention, to inactivate pathogens present in or on the material; and inclusion of compounds of the invention in targeted liposomes, to direct the compounds to particular cells in order to damage the nucleic acid of those cells.

It should be noted that while the compounds of the invention are designed to hydrolyze under certain conditions, they are stable under other conditions. It is desirable for the frangible linker and the effector group(s) to be relatively stable under certain conditions used for storage. Examples of manners in which the compounds may be stored include, but are not limited to, dry solids, oils with low water content, frozen aqueous solutions, frozen non-aqueous solutions, suspensions, and solutions which do not permit hydrolysis of the frangible linker or the effector group(s), for example liquid non-aqueous solutions. The compounds may be stored at temperatures at or below 0° C. (e.g., in a freezer), or at temperatures above 0° C. (e.g., in a refrigerator or at ambient temperatures). The compounds preferably are stable under the storage conditions for a period of between three days and one year, between one week and one year, between one month and one year, between three months and one year, between six months and one year, between one week and six months, between one month and six months, between three months and six months, between one week and three months, or between one month and three months. The stability of the compounds will be determined both by the temperature at which they are stored, and by the state in which they are stored (e.g., non-aqueous solution, dry solid).

Conditions for Pathogen Inactivation

Conditions for treating biological materials with a pathogen inactivating compound may be selected based on the selected material and the inactivating compound. Typical concentrations of pathogen inactivating compound for the treatment of biological materials such as blood products are on the order of about 0.1 $\mu$M to 5 mM, for example about 500 $\mu$M. For example, a concentration of pathogen inactivating compound may be used which is sufficient to inactivate at least about 1 log, or at least about 2 logs, or for example, at least about 3 to 6 logs of a pathogen in the sample. In one embodiment, the pathogen inactivating compound produces at least 1 log kill at a concentration of no greater than about 500 $\mu$M, more preferably at least 3 logs kill at no greater than 500 $\mu$M concentration. In another non-limiting example, the pathogen inactivating compound may have at least 1 log kill, and preferably at least 6 logs kill at a concentration of about 0.1 $\mu$M to about 3 mM.

Incubation of blood products with the pathogen inactivating compound can be conducted for example, for about 5 minutes to 72 hours or more, or about 1 to 48 hours, for example, about 1 to 24 hours, or, for example, about 8 to 20 hours. For red blood cells, the incubation is typically conducted at a temperature of about 2° C. to 37° C., preferably about 18° C. to 25° C. For platelets, the temperature is preferably about 20 to 24° C. For plasma, the temperature may be about 0 to 60° C., typically about 0–24° C. The pH of the material being treated is preferably about 4 to 10, more preferably about 6 to 8.

One embodiment of the invention encompasses compounds and methods for use in inactivating pathogens in blood or blood products, and a preferred set of storage conditions for this purpose would be those conditions that allow the convenient storage and use of the compounds at blood banks.

Under the conditions used for pathogen inactivation in or on a material, the frangible linker and effector group(s) will undergo hydrolysis or reaction. The hydrolysis, of both the frangible linker and the effector groups(s), preferably is slow enough to enable the desired amount of pathogen inactivation to take place. The time required for pathogen inactivation may be, for example, about 5 minutes to 72 hours.

Treatment of Red Blood Cells

Preferably, treatment of red blood cell containing materials with the pathogen inactivating compound does not damage red blood cell function or modify red blood cells after treatment. The lack of a substantially damaging effect on red blood cell function may be measured by methods known in the art for testing red blood cell function. For example, the levels of indicators such as intracellular ATP (adenosine 5'-triphosphate), intracellular 2,3-DPG (2,3-diphosphoglycerol) or extracellular potassium may be measured, and compared to an untreated control. Additionally hemolysis, pH, hematocrit, hemoglobin, osmotic fragility, glucose consumption and lactate production may be measured.

Methods for determining ATP, 2,3-DPG, glucose, hemoglobin, hemolysis, and potassium are available in the art. See for example, Davey et al., *Transfusion,* 32:525–528 (1992), the disclosure of which is incorporated herein. Methods for determining red blood cell function are also described in Greenwalt et al., *Vox Sang,* 58:94–99 (1990); Hogman et al., *Vox Sang,* 65:271–278 (1993); and Beutler et al., *Blood,* Vol. 59 (1982) the disclosures of which are incorporated herein by reference. Extracellular potassium levels may be measured using a Ciba Corning Model 614 $K^+/Na^+$ Analyzer (Ciba Coming Diagnostics Corp., Medford, Mass.). The pH can be measured using a Ciba Corning Model 238 Blood Gas Analyzer (Ciba Corning Diagnostics Corp., Medford, Mass.).

Binding of species such as IgG, albumin, and IgM to red blood cells also may be measured using methods available in the art. Binding of molecules to red blood cells can be detected using antibodies, for example to acridine and IgG. Antibodies for use in assays can be obtained commercially, or can be made using methods available in the art, for example as described in Harlow and Lane, "Antibodies, a Laboratory Manual, Cold Spring Harbor Laboratory," 1988, the disclosure of which is incorporated herein. For example, anti-IgG is commercially available from Caltag, Burlingame, Calif.; Sigma Chemical Co., St. Louis, Mo. and Lampire Biological Laboratory, Pipersvelle, Pa.

In a method of treatment of a material comprising red blood cells with the pathogen inactivating compound, preferably the level of extracellular potassium is not greater than 3 times, more preferably no more than 2 times the amount exhibited in the untreated control after 1 day. In another embodiment, preferably, hemolysis of the treated red blood cells is less than 3% after 28 day storage, more preferably less than 2% after 42 day storage, and most preferably less than or equal to about 1% after 42 day storage at 4° C.

Biological Materials

A variety of biological materials may be treated with a pathogen inactivating compound. Biological materials include blood products such as whole blood, packed red blood cells, platelets and fresh or frozen plasma. Blood products further encompass plasma protein portion, antihemophilic factor (Factor VIII), Factor IX and Factor IX complex, fibrinogens, Factor XIII, prothrombin and thrombin, immunoglobulins (such as IgG, IgA, IgD, IgE and IgM and fragments thereof), albumin, interferon, and lymphokines. Also contemplated are synthetic blood products.

Other biological materials include vaccines, recombinant DNA produced proteins and oligopeptide ligands. Also encompassed are clinical samples such as urine, sweat, sputum, feces, spinal fluid. Further encompassed are synthetic blood or blood product storage media.

Reducing the Concentration of Compounds in Materials after Treatment

The concentration of the pathogen inactivating compound in a biological material, such as a blood product, can be reduced after the treatment. Methods and devices which may be used are described in PCT/US96/09846; U.S. Ser. No. 08/779,830, filed Jan. 6, 1997; and in the co-filed application, "Methods and Devices for the Reduction of Small Organic Compounds from Blood Products", Ser. No. PCT/US98/00531, Attorney Docket No. 2000440, filed Jan. 6, 1998, the disclosures of each of which are incorporated herein by reference in their entirety.

Quenching

In another embodiment the compounds of the invention may be used in combination with a quencher. Methods for quenching undesired side reactions of pathogen inactivating compounds in biological materials are described in the cofiled U.S. Provisional Application Ser. No. 60/070,597, filed Jan. 6, 1998, Attorney Docket No. 282173000600, "Methods for Quenching Pathogen Inactivators in Biological Materials," the disclosure of which is incorporated herein. Disclosed in the cofiled application are methods for quenching undesired side reactions of a pathogen inactivating compound that includes a functional group which is, or which is capable of forming, an electrophilic group. In this embodiment, the material is treated with the pathogen inactivating compound and a quencher, wherein the quencher comprises a nucleophilic functional group that is capable of covalently reacting with the electrophilic group. Preferred quenchers are thiols, such as glutathione.

EXAMPLES

The following specific examples are presented to illustrate the preparative methods for representative compounds useful in the method of this invention, to provide relevant data regarding the compounds useful to the practitioner, and to illustrate the manner in which the effectivity of the compounds is determined, and are not to be construed as limiting the scope of the invention. All NMR spectra were recorded on a Varian 200 MHz instrument in $CDCl_3$ unless otherwise noted; chemical shifts are reported versus tetramethylsilane (TMS). IR spectra were recorded with a Perkin Elmer FTIR. HPLC was carried out with a YMC C8 column in a gradient mode using 5 mM aq. $H_3PO_4$ as mobile phase A and 5 mM $CH_3CN$ as mobile phase B. Samples were prepared in DMSO or ethanol and kept at $\leqq$15° C. prior to injection.

Table II indicates the designation of compound number used for the various compounds.

TABLE II

| COMPOUND NUMBER | CHEMICAL NAME |
|---|---|
| IV | β-alanine, N-(2-carbomethoxyacridin-9-yl), 2-[bis(2-chloroethyl)amino]ethyl ester |
| V | β-alanine, N-(acridin-9-yl), 2-[bis(2-chloroethyl)amino]ethyl ester |
| VI | 4-aminobutyric acid N-[(2-carbomethoxyacridin-9-yl), 2-[bis(2-chloroethyl)amino]ethyl ester |
| VII | 5-aminovaleric acid N-[(2-carbomethoxyacridin-9-yl), 2-[bis(2-chloroethyl)amino]ethyl ester |
| VIII | β-alanine, N-(2-carbomethoxyacridin-9-yl), 3-[bis(2-chloroethyl)amino]propyl ester |
| IX | β-alanine, N-(4-methoxyacridin-9-yl), 2-[bis(2-chloroethyl)amino]ethyl ester |
| X | β-alanine, N-(3-chloro-4-methylacridin-9-yl), 2-[bis(2-chloroethyl)amino]ethyl ester |
| XI | β-alanine, [N,N-bis(2-chloroethyl)], 3-[(6-chloro-2-methoxyacridin-9-yl)amino]propyl ester |
| XII | β-alanine, [N,N-bis(2-chloroethyl)], 2-[(6-chloro-2-methoxyacridin-9-yl)amino]ethyl ester |
| XIII | β-alanine, N-(6-chloro-2-methoxyacridin-9-yl), 2-[bis(2-chloroethyl)amino]ethyl ester |
| XIV | [N,N-bis(2-chloroethyl)]-2-aminoethyl 4,5',8-trimethyl-4'-psoralenacetate |
| XV | β-alanine, N-(acridin-9-yl), 2-[bis(2-chloroethyl)amino]ethyl amide |

Example 1

Synthesis of β-alanine, N-(2-carbomethoxyacridin-9-yl), 2-[bis(2-chloroethyl)amino]ethyl ester dihydrochloride (Compound IV,)

Step A. β-Alanine, N-(tert-butoxycarbonyl), 2-[bis(2-hydroxyethyl)amino]ethyl ester To a stirred solution of N-(tert-butoxycarbonyl)-β-alanine (20.3 g, 107 mmol) and 4-methylmorpholine (13.0 mL, 12.0 g, 119 mmol) in dry THF (200 mL) at −15° C. under $N_2$ was added isobutyl chloroformate (13.9 mL, 14.6 g, 107 mmol) resulting in the immediate formation of a white precipitate (4-methylmorpholine.HCl). The reaction mixture was stirred at −15° C. for 5 min. followed by the transfer of the reaction mixture to a flask containing a stirred solution of triethanolamine (48.3 g, 324 mmol) in dry THF (150 mL) at −15° C. The reaction mixture was allowed to warm to 23° C. and stirred for an additional 1.5 h. followed by removal of the precipitate by vacuum filtration. The THF was then removed in vacuo from the filtrate and the remaining viscous yellow oil was partitioned between water (500 mL) and EtOAc (5×150 mL). The combined organic layers were dried over $Na_2SO_4$. Removal of solvent in vacuo gave 25.8 g (75%) of the desired product, β-alanine, N-(tert-butoxycarbonyl), 2-[bis(2-hydroxyethyl)amino]ethyl ester, as a pale yellow oil. $^1$H NMR: δ 5.32 (br s, 1H), 4.18 (t, J=5.4 Hz, 2H), 3.58 (t, J=5.1 Hz, 4H), 3.37–3.23 (m, 2H), 2.80 (t, J=5.4 Hz, 2H), 2.69 (t, J=5.1 Hz, 4H), 2.51 (t, J=6.0 Hz, 2H), 1.41 (s, 9H) The hydroxyl protons were not observed. $^{13}$C NMR: δ 173.0, 156.4, 79.8, 63.3, 60.2, 57.3, 54.1, 36.7, 35.3, 28.8.

Step B. β-Alanine, N-(tert-butoxycarbonyl), 2-[bis(2-tert-butyldimethylsilyloxyethyl)amino]ethyl ester A stirred solution of the β-alanine, N-(tert-butoxycarbonyl), 2-[bis(2-hydroxyethyl)amino]ethyl ester from step A (22.7 g, 70.9 mmol) and imidazole (11.1 g, 163 mmol) in acetonitrile (70 mL) under $N_2$ was cooled to 0° C. Tert-butyldimethylsilyl chloride (534 mg, 3.54 mmol) was then added and the reaction mixture was stirred for an additional 5 min. at 0° C. The reaction mixture was allowed to warm to 23° C. and stirred for 2 h followed by removal of the resultant white precipitate (imidazole.HCl) by vacuum filtration. The acetonitrile was removed in vacuo from the filtrate and the remaining material was partitioned between saturated brine (600 mL) and EtOAc (3×200 mL). The combined organic layers were dried over $Na_2SO_4$. Removal of solvent in vacuo gave 35.2 g (90%) of the desired product, β-alanine, N-(tert-butoxycarbonyl), 2-[bis(2-tert-butyldimethylsilyloxyethyl)amino]ethyl ester, as a yellow oil. $^1$H NMR: δ 5.29 (br s, 1 H), 4.14 (t, J=6.0 Hz, 2H), 3.65 (t, J=6.3 Hz, 4H), 3.37 (apparent q, 2H), 2.85 (t, J=6.0 Hz, 2H), 2.71 (t, J=6.3 Hz, 4H), 2.49 (t, J=5.9 Hz, 2H), 1.42 (s, 9H), 0.88 (s, 18 H), 0.03 (s, 12H); $^{13}$C NMR: δ 172.7, 156.3, 79.7, 63.3, 62.4, 57.7, 54.3, 36.7, 35.3, 28.9, 26.4, 18.7, −4.9.

Step C. β-Alanine, 2-[bis(2-tert-butyldimethylsilyloxyethyl)amino]ethyl ester

To a flask containing β-alanine, N-(tert-butoxycarbonyl), 2-[bis(2-tert-butyldimethylsilyloxyethyl)amino]ethyl ester from step B (3.01 g, 5.48 mmol) was added neat trifluoroacetic acid (5 mL) resulting in the evolution of $CO_2$ gas. The reaction mixture was stirred for 5 min. and the trifluoroacetic acid was removed in vacuo. The remaining material was partitioned between saturated $NaHCO_3$ (100 mL) and EtOAc (3×30 mL). The combined organic layers were dried over $Na_2SO_4$. Removal of solvent in vacuo gave 2.45 g (100%) of the desired product, β-alanine, 2-[bis(2-tert-butyldimethylsilyloxyethyl)amino]ethyl ester, as a pale yellow oil. $^1$H NMR: δ 4.12 (t, J=6.0 Hz, 2H), 3.63 (t, J=6.4 Hz, 4H), 2.96 (t, J=6.2 Hz, 2H), 2.84 (t, J=6.0 Hz, 2 H), 2.69 (t, J=6.4 Hz, 4H), 2.44 (t, J=6.2 Hz, 2H), 0.86 (s, 18H), 0.03 (s, 12H). The amine protons were not observed. $^{13}$C NMR ($CDCl_3$): δ 173.0, 63.4, 62.6, 57.9, 54.4, 38.4, 38.1, 26.4, 18.7, −4.9.

Step D. β-Alanine, N-(2-carbomethoxyacridin-9-yl), 2-[bis(2-hydroxyethyl)amino]ethyl ester The β-alanine, 2-[bis(2-tert-butyldimethylsilyloxyethyl)amino]ethyl ester (736 mg, 1.64 mmol) was reacted with methyl 9-methoxyacridine-2-carboxylate (669 mg, 2.50 mmol) by stirring in 10 mL of $CHCl_3$ for 12.5 h at room temperature. The precipitate (acridone) was then filtered off and the filtrate partitioned between saturated aqueous $NaHCO_3$ (100 mL) and $CHCl_3$ (3×35 mL). The combined organic layers were dried over $Na_2SO_4$ and concentrated in vacuo to give 1.61 g of viscous brown oil. Deprotection of the resultant diol was carried out by dissolving the crude intermediate in 3.0 mL of THF under $N_2$ and, upon cooling to 0° C., treating with HF/pyridine (1.0 mL). The solution was allowed to warm to room temperature with stirring for 1 h. The volatiles were removed in vacuo and the residue was partitioned between saturated aqueous $NaHCO_3$ (100 mL) and $CHCl_3$ (3×35 mL). The combined organic layers were dried and concentrated to give 649 mg of a brownish yellow solid. Preparative TLC (C-18, $CH_3CN$) gave a 20% yield of the desired diol, β-alanine, N-(2-carbomethoxyacridin-9-yl), 2-[bis(2-hydroxyethyl)amino] ethyl ester (>80% pure by HPLC); $^1$H NMR: δ 8.82 (s, 1H), 8.21–7.94 (m, 2H), 7.94–7.72 (m, 2H), 7.59 (apparent t, 1H), 7.23 (apparent t, 1H), 4.30–4.18 (m, 2H), 4.18–4.05 (m, 2H), 3.89 (s, 3H), 3.69–3.50 (m, 4H), 2.92–2.73 (m, 4H), 2.73–2.55 (m, 4H) The amine and hydroxyl protons were not observed.

Step E. β-Alanine, N-(2-carbomethoxyacridin-9-yl), 2-[bis (2-chloroethyl)amino]ethyl ester dihydrochloride Conversion of β-alanine, N-(2-carbomethoxyacridin-9-yl), 2-[bis(2-hydroxyethyl)amino]ethyl ester to the dichloro compound was achieved by a method similar to that of Peck, et al. (*J. Am. Chem. Soc.* 1959, 81: 3984). A yellow solution of the product from step D (41 mg, 0.090 mmol) in neat $SOCl_2$ (6 mL) was stirred at room temperature for 20 hours. The $SOCl_2$ was then removed in vacuo to give a yellow solid (dihydrochloride salt). The material was then partitioned between saturated $NaHCO_3$ (50 mL) and $CH_2Cl_2$ (3×20 mL). The combined organic layers were dried over $Na_2SO_4$. Removal of solvent in vacuo gave 35.4 mg of the dichloro compound free base as an orange gum. $^1$H NMR: δ 8.82 (s, 1H), 8.20–7.83 (m, 4H), 7.5 (apparent t, 1H), 7.25 (apparent t, 1H), 4.36–4.15 (m, 4H), 3.93 (s, 3H), 3.48 (t, J=6.9 Hz, 4H), 3.06–2.77 (m, 4H), 2.86 (t, J=6.9 Hz, 4H) The amine proton was not observed. $^{13}$C NMR: δ 172.3, 166.6, 155.2, 146.5, 144.6, 133.1, 131.6, 128.7, 124.6, 124.3, 116.1, 114.3, 63.7, 57.2, 53.5, 52.9, 46.3, 42.5, 35.2. No other carbons were observed. The HCl salt was precipitated from $CH_2Cl_2$ by addition of 1 M HCl in ether to give β-alanine, N-(2-carbomethoxyacridin-9-yl), 2-[bis(2-chloroethyl) amino]ethyl ester dihydrochloride (Compound IV,) as a yellow solid (81% pure by HPLC).

β-Alanine, N-(acridin-9-yl), 2-[bis(2-chloroethyl)amino] ethyl ester dihydrochloride, (Compound V) was prepared in a similar manner. Thus using 9-methoxyacridine in place of methyl 9-methoxyacridine-2-carboxylate in Step D, the intermediate diol was obtained (7.1%) as a yellow oil (74% pure by HPLC). $^1$H NMR: δ 8.14 (d, J=7.5 Hz, 2H), 7.93 (d, J=8.6 Hz, 2H), 7.52 (apparent t, 2H), 7.23 (apparent t, 2H), 4.36–4.08 (m, 4H), 3.76–3.5 (m, 4H), 3.08–2.60 (m, 8H) The amine and hydroxyl protons were not observed.

A solution of the intermediate diol (37.3 mg, 0.0793 mmol) in thionyl chloride (4.0 mL) was stirred at 23° C. for 7.5 h. The thionyl chloride was removed in vacuo to give a yellow oil. The material was dissolved in ethanol (~4 mL) and the solvent removed in vacuo. The material was then dissolved in $CH_2Cl_2$ (4 mL) and solvent removed in vacuo; this step was repeated twice. The material was then triturated with hexane (3×4 mL) to give 40.0 mg (42% pure by HPLC) of the product in the form of a yellow hydroscopic glassy solid. Some of the material was converted to the free amine for analytical purposes by partitioning between saturated $NaHCO_3$ and $CH_2Cl_2$ followed by drying the combined organic layers over $Na_2SO_4$ and removal of the solvent in vacuo. $^1$H NMR: δ 8.21–8.00 (m, 4H), 7.66 (apparent t, 2H), 7.38 (apparent t, 2H), 4.26–4.12 (m, 2H), 4.12–3.98 (m, 2H), 3.43 (t, J=6.9 Hz, 4H), 2.96–2.68 (m, 8H) The amine proton was not observed.

Following the above procedure but replacing N-(tert-butoxycarbonyl)-β-alanine with N-(tert-butoxycarbonyl)-4-aminobutyric acid led to the preparation of 4-aminobutyric acid N-[(2-carbomethoxyacridin-9-yl), 2-[bis(2-chloroethyl)amino]ethyl ester dihydrochloride, Compound VI (78% pure by HPLC). $^1$H NMR: δ 8.89 (s, 1), 8.12 (apparent t, 2), 7.93–7.80 (m, 2), 7.59 (apparent q, 1), 7.36–7.20 (m, 1), 4.16 (t, 2, J=5.7 Hz), 4.07–3.92 (m, 2), 3.97 (s, 3), 3.46 (t, 4, J=6.9 Hz), 2.93–2.80 (m, 6), 2.60 (t, 2, J=6.5 Hz), 2.29–2.12 (m, 2). The amine proton was not observed.

Example 2

Substituting the triethanolamine in Example 1, Step A with 3-[N,N-Bis(2-tert-butyldimethylsilyloxyethyl)] aminopropanol, and then continuing from step C, led to the preparation of β-alanine, N-(2-carbomethoxy-acridin-9-yl), 3-[bis(2-chloroethyl)amino]propyl ester dihydrochloride, Compound VIII, (63% pure by HPLC). $^1$H NMR: δ 8.91 (s, 1), 8.20–7.93 (m, 4), 7.18 (apparent t, 1), 7.39 (apparent t, 1), 4.30 (m, 4), 3.96 (s, 3), 3.48 (t, 4, J=6.9 Hz), 2.88–2.60 (m, 2), 2.83 (t, 4, J=6.9 Hz), 2.62 (t, 2, J=6.7 Hz), 1.85–1.68 (m, 2) The amine proton was not observed.

Example 3

The compounds synthesized in Example 1 can also be prepared by the following method: Synthesis of β-alanine, N-(acridin-9-yl), 2-[bis(2-chloroethyl)amino]ethyl ester dihydrochloride (Compound V): Method II Step A: β-Alanine, N-(acridin-9-yl), methyl ester hydrochloride 9-Chloroacridine (11.7 g, Organic Synthesis, Coll. Vol III, pg 57), β-alanine methyl ester hydrochloride (9.9 g) and sodium methoxide (3.26 g) were combined and 60 mL of methanol was added. The mixture was stirred with a magnetic stirrer and refluxed for 5.5 h. Heat was removed and the suspension was filtered while warm (≦35° C.). The solid salts were rinsed with about 10 mL of additional methanol and the combined dark green filtrate was concentrated to give 21 g of a moist greenish-yellow solid.

The solid was dissolved in 350 mL of boiling 2-propanol and allowed to crystallize at room temperature. The resulting crystals were rinsed with about 15 mL of 2-propanol and 15 mL of hexane, then air dried to give 15.5 g of bright yellow product, β-alanine, N-(acridin-9-yl), methylester hydrochloride, (yield 78.5%). $^1$H NMR: δ 1.9 (br s, 2H); 3.24 (t, J=7.0 Hz, 2H); 3.76 (s, 3H); 4.45 (br s, 2H); 7.23 (app. t, J=8 Hz, 2H); 7.49 (app. t, J=8 Hz, 2H); 8.11 (d, J=8.4 Hz, 2H); 8.30 (d, J=8.4 Hz, 2H); 9.68 (br s, 0.5 H). IR: 1574 (s), 1691 (s), 1726 (s), 2336 (m), 2361 (m), 3227 (m).

Step B: β-Alanine, N-(acridin-9-yl), 2-[bis(2-hydroxyethyl) amino]ethyl ester dihydrochloride The β-alanine, N-(acridin-9-yl), methyl ester hydrochloride, from Step A, (5.00 g) was partitioned between toluene (750 mL), saturated aqueous $Na_2CO_3$ (200 mL) and $H_2O$ (50 mL). The aqueous layer was extracted again with toluene (3×250 mL) and the organic layers were combined and washed with saturated aqueous $Na_2CO_3$ (50 mL). The volume of toluene was reduced to about 100 mL by rotary evaporation. Triethanolamine (30 mL) was then added to form a partially immiscible system. A solution of NaOMe (50 mg) in MeOH (2 mL) was then added. Solvents were quickly removed from the reaction mixture by rotary evaporation with agitation at room temperature. After the solvent was removed the reaction mixture was left under vacuum for another 1–1.5 h to give a syrupy solution.

The crude mixture was partitioned between $CH_2Cl_2$ (200 mL) and brine (200 mL) to remove excess triethanolamine. The brine layer was extracted with $CH_2Cl_2$ (5×100 mL). The organic layers were combined and washed with brine (50 mL) then extracted with 0.5M HCl (2×100 mL). The aqueous acid layers were combined and washed with $CH_2Cl_2$ (50 mL). The acid solution was made basic with powdered $K_2CO_{3(s)}$ in the presence of $CH_2Cl_2$ (200 mL). The organic layer was separated and the aqueous layer was extracted again with $CH_2Cl_2$ (5×100 mL). The combined organic layers were washed with brine (50 mL), dried with anhydrous $Na_2SO_{4(s)}$, and stripped to give crude diol free amine (5.02 g), a sticky yellow gum. This material was identical by NMR to that prepared in Example 1 by an alternate procedure.

A portion of the above crude (0.400 g) was vigorously stirred with isopropanol (100 mL) and acidified with 1 M HCl in ether. The slurry was chilled and the first precipitate was discarded. After removing half the solvent the second set of crystals gave β-alanine, N-(acridin-9-yl), 2-[bis(2-hydroxyethyl)amino]ethyl ester dihydrochloride as a bright yellow crystalline solid (0.200 g) >95% pure by HPLC. $^1H$ NMR: δ 8.11 (apparent t, 4H), 7.69 (apparent t, 2H), 7.41 (apparent t, 2H), 4.23 (t, J=5.4 Hz, 2H), 4.03 (t, J=5.9 Hz, 2H), 3.58 (t, J=5.2 Hz, 4H), 2.73 (t, J=5.4 Hz, 2H), 2.70 (t, J=5.9 Hz, 2H) 2.68 (t, J=5.2 Hz, 4H). The amine and hydroxyl protons were not observed. $^{13}C$ NMR: δ 173.3, 151.7, 149.4, 130.5, 129.5, 124.0, 123.4, 118.4, 63.5, 60.1, 57.3, 54.0, 46.6, 35.8.

Step C: β-Alanine, N-(acridin-9-yl), 2-[bis(2-chloroethyl) amino]ethyl ester dihydrochloride $SOCl_2$ (0.5 ml) was added to a stirred suspension of β-alanine, N-(acridin-9-yl), 2[bis(2-hydroxyethyl)amino]ethyl ester dihydrochloride from Step B (113 mg, 0.24 mmol) in $CH_3CN$ (0.5 mL). The resultant yellow solution was stirred at 23° C. for 16 h followed by removal of the volatiles in vacuo. The remaining orange oil was dissolved in EtOH (~2 mL) and the EtOH was removed in vacuo to give a yellow solid. The material was then triturated with hexane (2×3 mL). Removal of residual solvents in vacuo gave 123 mg of the desired material, β-alanine, N-(acridin-9-yl), 2-[bis (2-chloroethyl)amino]ethyl ester dihydrochloride, (93% pure by HPLC) as a yellow solid. $^1H$ NMR: δ 8.09 (apparent t, J=8.8 Hz, 4H), 7.66 (apparent t, J=7.6 Hz, 2H), 7.38 (apparent t, J=7.7 Hz, 2H), 4.14 (t, J=5.9 Hz, 2H), 4.00 (t, J=5.8 Hz, 2H), 3.43 (t, J=6.9 Hz, 4H), 2.87 (t, J=6.9 Hz, 4H), 2.77 (t, J=5.9Hz, 2H), 2.69 (t, J=5.8 Hz, 2H). The amine proton was not observed. $^{13}C$ NMR: δ 173.0, 151.5, 149.4, 130.5, 129.6, 124.1, 123.4, 118.6, 63.5, 57.3, 53.5, 46.7, 42.5, 35.7. IR (KBr pellet of HCl salt): 3423, 3236, 2939, 2879, 1736, 1634, 1586, 1572, 1540, 1473, 1272, 1173 $cm^{-1}$.

Example 4

β-alanine, N-(4-methoxy-acridin-9-yl), 2-[bis(2-chloroethyl)amino]ethyl ester dihydrochloride, Compound IX.

β-alanine, N-(4-methoxy-acridin-9-yl), methyl ester was prepared by mixing 1.4 g (5.84 mmol) of 4,9-dimethoxyacridine, 0.89 g (6.42 mmol) of β-alanine methyl ester hydrochloride and 20 ml of methanol and then heating to reflux for 12 h under $N_2$. The reaction was then concentrated in vacuo, dissolved in $CHCl_3$-isopropanol (50 ml, 4:1 v/v), and washed with 50% $NH_4OH$ (2×25 ml) and brine (1×25 ml). The organic layer was dried with $Na_2SO_4$ and concentrated in vacuo to yield 1.24 g (68%) of the methyl ester (>74% purity by HPLC) as a yellow oil; $R_f$ (SiO2, ethyl acetate)=0.25; IR (thin film): 3363, 2947, 1730, 1611, 1573, 1518, 1484, 1463, 1423, 1420, 1246, 1170, 1081 $cm^{-1}$; $^1H$ NMR: δ 2.70 (t, 2H, J=5.7 Hz), 3.74 (s, 3H), 4.00 (t, 2H, J=6.3 Hz), 4.11 (s, 3H), 6.98 (d, 1H, J=7.4 Hz), 7.36 (m, 2H), 7.65 (m, 2H), 8.12 (d, 2H, J=8.5 Hz); $^{13}C$ NMR): δ 35.7, 46.9, 52.3, 56.5, 107.2, 115.3, 119.8, 123.5, 124.1, 130.0, 151.4, 173.6.

This was converted to the diol under conditions described in Example 3, Step B to afford 647 mg of a yellow oil. HPLC analysis of the crude mixture indicated a yield of 85% (λ=278 nm); $R_f$ (SiO2, 20% methanol-ethyl acetate)=0.17; IR (thin film): 3337, 2947, 2828, 1726, 1616, 1569, 1522, 1484, 1463, 1420, 1348, 1250, 1174, 1127, 1081, 1043 $cm^{-1}$; $^1H$ NMR: δ 2.7 (m, 8H), 3.55 (m, 4H), 3.97–4.08 (m, 2H), 4.08 (s, 3H), 4.19 (t, 2H, J=5.5 Hz), 6.96 (d, 1H, J=7.4 Hz), 7.29 (m, 2H), 7.61 (m, 2H), 8.10 (m, 2H); $^{13}C$ NMR: δ 36.0, 46.9, 53.7, 56.4, 57.1, 60.1, 63.3, 107.4, 115.7, 119.1, 119.6, 123.2, 123.5, 123.9, 128.5, 130.0, 140.8, 147.4, 151.6, 151.7, 154.3, 173.3.

This was converted to β-alanine, N-(4-methoxy-acridin-9-yl), 2-[bis(2-chloroethyl)amino]ethyl ester dihydrochloride with thionyl chloride as described in Example 3, Step C. Flash filtration ($SiO_2$) of the crude product using ethyl acetate followed by 10% methanol-ethyl acetate gave 58 mg of a yellow oil after apparent on-column degradation of some product; $R_f$ (SiO2, ethyl acetate)=0.26; IR (thin film): 3405, 2955, 2828, 1726, 1616, 1577, 1518, 1463, 1416, 1348, 1246, 1174, 1123, 1081, 1013 $cm^{-1}$; $^1H$ NMR: δ 2.69–2.99 (m, 8H), 3.45 (t, 4H, J=6.7 Hz), 4.03 (m, 2H), 4.09 (s, 3H), 4.16 (t, 2H, J=5.9 Hz), 6.97 (d, 1H, J=7.7 Hz), 7.32 (m, 2H), 7.65 (m, 2H), 8.12 (d, 2H, J=8.7 Hz).

The dihydrochloride salt could be isolated in crude form by concentrating the reaction in vacuo with azeotropic removal of excess thionyl chloride (2×5 ml toluene). HPLC analysis indicated complete consumption of the starting material and 4-methoxy acridone ($R_T$=22.3 min) to be the major impurity. $^1H$ NMR ($CD_3OD$): δ 3.18 (t, 2H, J=6.4 Hz), 3.71 (m, 6H), 4.04 (m, 4H), 4.18 (s, 3H), 4.51 (m, 2H), 7.17 (m, 2H), 7.56 (m, 2H), 7.91–8.15 (m, 2H), 8.55 (d, 1H, J=8.8 Hz).

Similarly prepared from 3-chloro-9-methoxy-4-methylacridine was β-alanine, N(3-chloro-4-methylacridin-9-yl), 2-[bis(2-chloroethyl)amino]ethyl ester dihydrochloride, Compound X. $^1H$ NMR of the free base: δ 7.96–8.17 (m, 3H), 7.29–7.52 (m, 3H), 4.19 (t, J=5.8 Hz, 2H), 4.00 (s, 3H), 3.89 (t, J=5.1 Hz, 2H), 3.47 (t, J=6.8 Hz, 4H), 2.91 (t, J=6.8 Hz, 4H), 2.83 (t, J=5.8 Hz, 2H), 2.67 (t, J=5.5 Hz, 2H).

Similarly prepared from 6-chloro-2,9-dimethoxyacridine was β-alanine, N-(6-chloro-2-methoxyacridin-9-yl), 2-[bis (2-chloroethyl)amino]ethyl ester dihydrochloride, Compound XIII. $^1H$ NMR of the free base: δ 7.96–8.17 (m, 3H), 7.29–7.52 (m, 3H), 4.19 (t, J=5.8 Hz, 2H), 4.00 (s, 3H), 3.89 (t, J=5.1 Hz, 2H), 3.47 (t, J=6.8 Hz, 4H), 2.91 (t, J=6.8 Hz, 4H), 2.83 (t, J=5.8 Hz, 2H), 2.67 (t, J=5.5 Hz, 2H).

Example 5

β-alanine, [N,N-bis(2-chloroethyl)], 3-[(6-chloro-2-methoxyacridin-9-yl)amino]propyl ester dihydrochloride, Compound XI.

Step A β-Alanine, [N,N-bis(2-triisopropylsilyloxy)ethyl] ethyl ester

A slurry of β-alanine ethyl ester hydrochloride (1.99 g, 12.9 mmol), $K_2CO_3$ (6.0 g, 43.4 mmol) and iodoethyl triisopropylsilyl ether (9.47 g, 28.9 mmol) in acetonitrile (175 mL) were refluxed for 5–7 days. After vacuum evaporation of the solvent, the solid was triturated with $CH_2Cl_2$. The organic layer was washed with dilute $Na_2CO_{3(aq)}$, then with brine and dried over anhydrous $Na_2SO_4$. The crude product was purified by silica gel chromatography (1:4 EtOAc/hexane) to provide 5.60 g of the oil, β-alanine, [N,N-bis(2-triisopropylsilyloxy)ethyl]ethyl ester, (83.1%). $^1$H NMR: δ 4.12 (q, J=7.1 Hz, 2H), 3.73 (t, J=6.8 Hz, 4H), 2.92 (t, J=7.3 Hz, 2H), 2.70 (t, J=6.6 Hz, 4H), 2.46 (t, J=7.4 Hz, 2H), 1.4–0.9 (m, 45H, includes triplet at 1.25 (3H) and singlets at 1.06 and 1.05).

Step B β-Alanine, N,N-bis(2-triisopropylsilyloxy)ethyl

The β-alanine, [N,N-bis(2-triisopropylsilyloxy)-ethyl] ethyl ester from Step A above (5.60 g, 10.8 mmol) and lithium hydroxide (0.59 g, 14.1 mmol) were stirred in ethanol and refluxed for 3 h. The solvent was removed and the crude product was partitioned between $CH_2Cl_2$ and dilute $NaHCO_{3(aq)}$. The organic layer was washed with brine, dried over anhydrous $Na_2SO_4$, and stripped to give β-alanine, N,N-bis(2-triisopropylsilyloxy)ethyl as a pale yellow oil (5.03 g, 95.1% yield). $^1$H NMR: δ 3.90 (t, J=5.5 Hz, 4H), 3.04 (t, J=6.2 Hz, 2H), 2.92 (t, J=5.5 Hz, 4H), 2.50 (t, J=6.1 Hz, 2H), 1.06 (s, 42H).

Step C β-Alanine, [N,N-bis(2-hydroxyethyl)], 3-[(6-chloro-2-methoxyacridin-9-yl)amino]propyl ester The β-alanine, N,N-bis(2-triisopropylsilyloxy)ethyl from Step B above (51.0 mg, 0.104 mmol) was stirred under $N_2$ in $CH_2Cl_2$ (1 mL). While chilling on an ice bath, $SOCl_2$ (0.5 mL) was added dropwise and the reaction was stirred for 2.25 h. After stripping the reaction mixture to remove excess $SOCl_2$, dry $CH_2Cl_2$ (0.5 mL) was added and the solution was chilled in an ice bath while under $N_2$. A chilled slurry of 9-(3-hydroxy)propylamino-6-chloro-2-methoxy-acridine (29.0 mg, 91.5 mmol) in $CH_2Cl_2$ (1 mL) was added. After 0.5 h the mixture was partitioned between $CH_2Cl_2$ and aqueous $NaHCO_3$. The organic layer was washed with brine, dried with anhydrous $Na_2SO_4$, and stripped. The gum obtained was triturated with hexane and the hexane extract was stripped to obtain a very crude mixture (53.5 mg) of triisopropylsilyl protected starting material and product.

To remove the triisopropylsilyl groups, a portion of the crude protected diol (33.1 mg) was stirred in ice cold THF (1 mL). After the addition of HF/pyridine (0.5 mL) the mixture was stirred at ambient temperature under a $N_2$ filled balloon for 2.5 h. The reaction mix was partitioned between $CH_2Cl_2$ and $NaHCO_{3(aq)}$ and the organic layer was washed several times with dilute $NaHCO_{3(aq)}$ to remove excess HF/pyridine. After preliminary drying with brine, then with anhydrous $Na_2SO_4$, the solvent was stripped off to give crude diol (13.1 mg).

This was combined with additional crude diol (5.0 mg) and purified by C-18 preparative TLC with 95 $CH_2Cl_2$/5 iPA/1 TFA as eluent to obtain the diol TFA salt. After partitioning the salt between $CH_2Cl_2$ and $NaHCO_{3(aq)}$, the organic layer was dried with brine, then with anhydrous $Na_2SO_4$, and stripped to give the free base of the diol, β-alanine, [N,N-bis(2-hydroxyethyl)], 3-[(6-chloro-2-methoxyacridin-9-yl)amino]propyl ester, (5.0 mg). $^1$H NMR: δ 7.92–8.25 (m, 3H), 7.23–7.47 (m, 3H), 4.30 (t, J=5.7 Hz, 2H)), 3.98 (s, 3H), 3.81 (t, J=6.2 Hz, 2H), 3.64 (t, J=4.9 Hz, 4H), 2.86 (t, J=6.1 Hz, 2H), 2.67 (t, J=4.9 Hz, 4H), 2.51 (t, J=5.9 Hz, 2H), 2.04 (apparent quintet, 2H).

Step D β-Alanine, [N,N-bis(2-chloroethyl)], 3-[(6-chloro-2-methoxyacridin-9-yl)amino]propyl ester dihydrochloride, Compound XI.

The β-alanine, [N,N-bis(2-hydroxyethyl)], 3-[(6-chloro-2-methoxyacridin-9-yl)amino]propyl ester from above (4.0 mg, 0.0073 mmol) was dissolved in $CH_2Cl_2$ (1 mL) and chilled in an ice/water bath. Ice cold $SOCl_2$ (0.1 mL) was added and the reaction was allowed to stir for 4 h at room temperature. The reaction mixture was stripped to remove solvent, triturated with hexane, and partitioned between $CH_2Cl_2$ and $NaHCO_{3(aq)}$. After the organic layer was dried with brine, then with anhydrous $Na_2SO_4$ and stripped, the dichloro- compound was obtained as a yellow gum. $^1$H NMR: δ 7.8–8.2 (m, 3H), 7.2–7.5 (m, 3H), 4.35 (t, J=5.9 Hz, 2H), 3.85–4.10 (3.99, s, OMe and 3.9–4.0, m, N<u>HCH</u>$_2$, total 5H), 3.48 (t, J=6.9 Hz, 4H), 2.9–3.0 (m, 6H), 2.49 (t, J=6.6 Hz, 2H), 2.1–2.3 (m, 2H).

The free amine was stirred in chilled $CH_2Cl_2$, acidified with 1M HCl in ether and stripped with a few drops of methanol to obtain the desired compound, β-alanine, [N,N-bis(2-chloroethyl)], 3-[(6-chloro-2-methoxyacridin-9-yl) amino]propyl ester dihydrochloride (2.5 mg), (3.5 mg, 81%), as a yellow solid.

In the same manner as given in the foregoing Step C, but using 6-chloro-9-(2-hydroxy)ethylamino-2-methoxy-acridine instead of 6-chloro-9-(3-hydroxy)propylamino-2-methoxy-acridine, was prepared the analogous diol. $^1$H NMR: δ 7.96–8.13 (m, 3H), 7.20–7.47 (m, 3H), 4.76 (t, J=4.9 Hz, 2H), 3.99 (s, 3H), 3.92–4.14 (m, 2H), 3.60 (t, J=5.1 Hz, 4H), 2.78 (t, J=6.1 Hz, 2H), 2.63 (t, J=5.1 Hz, 4H), 2.45 (t, J=6.0 Hz, 2H). By analogy to Step D this was converted to β-alanine, [N,N-bis(2-chloroethyl)], 2-[(6-chloro-2-methoxyacridin-9-yl)amino]ethyl ester dihydrochloride, Compound XII. $^1$H NMR: δ 7.94–8.20 (m), 7.20–7.50 (m), 4.42 (<u>CH</u>$_2$OC=O), 3.90–4.10 (O<u>CH</u>$_3$, NH<u>CH</u>$_2$), 3.46 (<u>CH</u>$_2$Cl), 2.82 (N(<u>CH</u>$_2$)$_3$), 2.39–2.56 (<u>CH</u>$_2$C=O).

Example 6

[N,N-Bis(2-chloroethyl)]-2-aminoethyl 4,5',8-trimethyl-4'-psoralenacetate hydrochloride, Compound XIV Step A: [N,N-Bis(2-hydroxyethyl)]-2-aminoethyl 4,5',8-trimethyl-4'0-psoralenacetate A slurry of methyl 4,5',8-trimethyl-4'-psoralenacetate (250 mg, 0.832 mmol), triethanolamine (12 mL) and 1M HCl in ether (2 mL) were stirred at 100° C. for 2 h. The resulting clear brown solution was allowed to cool to room temperature and partitioned between $CH_2Cl_2$ and saturated $NaHCO_{3(aq)}$. The organic layer was rinsed several times with saturated $NaHCO_{3(aq)}$. After drying with anhydrous $Na_2SO_4$, solvent was removed in vacuo and the residue was partitioned between $CH_2Cl_2$ and 1M aq. HCl. The aqueous layer was rinsed several times with $CH_2Cl_2$ and then made basic with $K_2CO_3$(s) in the presence of the organic solvent. The organic layer containing the neutral product was rinsed with water several times, then dried and concentrated. A repetition of the acid-base extraction procedure gave the desired product as a beige solid (84.3 mg, 24.3%): $^1$H NMR: δ 7.53 (s, 1H), 6.24 (s, 1H), 4.23 (t, J=5.4 Hz, 2H), 3.69 (s, 2H), 3.56 (t, J=5.3 Hz, 4H), 2.82 (t, J=5.4 Hz, 2H), 2.69 (t, J=5.3 Hz, 4H), 2.57 (s, 3H), 2.51 (d, J=1.1 Hz, 3H), 2.47 (s, 3H).

Step B: [N,N-Bis(2-chloroethyl)]-2-aminoethyl 4,5',8-trimethyl-4'-psoralenacetate hydrochloride Thionyl chloride (0.2 mL) was added to an ice cold mixture of the above diol (9.8 mg, 0.023 mmol) in $CH_2Cl_2$ (1 mL) and stirred at room temperature overnight under nitrogen. The resulting slurry was concentrated then triturated with hexane to give the desired product (6.2 mg, 53.9%) as an off-white solid: $^1$H NMR ($CD_3OD$): δ 7.71 (s, 1H), 6.28 (s, 1H), 4.56 (t, J=4.8 Hz, 2H), 3.95 (t, J=6.1 Hz, 4H), 3.89 (s, 2H), 3.60–3.83 (m, 6H), 2.54 (s, 3H), 2.53 (s, 3H), 2.50 (s, 3H).

Example 7

Synthesis of β-alanine, N-(acridin-9-yl), 2-[bis(2-chloroethyl)amino]ethyl amide (Compound XV)

Step A 2-[N',N'-Bis(2-hydroxyethyl)]-N-(tert-butoxycarbonyl)ethylenediamine

To a solution of N-(tert-butoxycarbonyl)ethanolamine (1.21 g, 7.5 mmol) and triethylamine (1.57 mL, 1.1 g, 11 mmol) in dry $CH_2Cl_2$ (25 mL) at 0° C. was added methanesulfonyl chloride (0.64 mL, 0.95 g, 8.3 mmol) dropwise. The reaction was stirred at 0° C. for 1 h, allowed to warm to 23° C. and was stirred overnight. The volatiles were removed in vacuo to give the mesylate as a white solid. Diethanolamine (7.2 mL, 7.9 g, 75 mmol) was added and the reaction mixture was heated to 75° C. with stirring for 6 h. The crude reaction mixture was partitioned between $H_2O$ (60 mL) and $CHCl_3$ (4×20 mL). The combined organic layers were washed with brine (20 mL) and dried over $Na_2SO_4$. Removal of solvent in vacuo gave 1.21 g (65%) of the diol as a thick-yellow oil, $^1$H NMR: δ 5.51–5.39 (m, 1H), 3.61 (t, J=4.9 Hz, 4H), 3.29–3.13 (m, 2H), 2.68–2.52 (m, 6H), 1–44 (s, 9H). The hydroxyl protons were not observed, Step B 2-[N',N'-Bis(2-tert-butyldimethylsilyloxyethyl)]-N-(tert-butoxycarbonyl)ethylenediamine To a stirred solution of the diol from step A (1.21 g, 4.87 mmol) and pyridine (1.59 mL, 1.55 g, 19.6 mmol) in dry $CH_2CL_2$ (12 mL) at 0° C. was added tert-butyldimethylsilyl chloride (2.21 g, 14.7 mmol). The reaction mixture was allowed to warm to 23° C. and was stirred for 2 d. The reaction mixture was diluted with $CH_2Cl_2$ (80 mL) and washed with $H_2O$ (3×25 mL) and then brine (3×25 mL). The organic layer was dried over $Na_2SO_4$. Removal of solvent in vacuo) gave 2.26 g (97%) of a pale yellow oil. $^1$H NMR: δ 5.37–5.22 (m, 1H), 3.62 (t, J=6.2 Hz, 4H), 3.19–3.08 (m, 2H) 2.63 (t, J=6.2 Hz, 6H), 1.42 (s, 9H), 0.873 (s, 18H), 0.04 (s, 12H).

Step C 2-[N,N,Bis(2,tert-butyldimethylsilyloxyethyl)] ethylenediamine

To a flask containing the protected amine from step B (4.24 g, 8.89 mmol) was added 5 mL of trifluoroacetic acid at 23° C. The reaction mixture was stirred for 15 minutes at 23° C. followed by removal of the trifluoracetic acid in vacuo. The crude product was partitioned between 2 N NaOH (100 mL) and $CH_2Cl_2$ (3×35 mL). The combined organic layers were dried over $Na_2SO_4$. Removal of solvent in vacuo gave 1.76 g (53%) of a yellow oil. $^1$H NMR: δ 3.66 (t, J=6.5 Hz, 4H), 2.72–2.53 (m, 8H), 1.72–1.63 (m, 2H), 0.87 (s, 18H), 0.02 (s, 12H).

Step D β-4Alanine, N-(tert-butoxycarbonyl), 2-[bis(2-tert-butyldimethylsilyloxyethyl)amino]ethyl amide To a solution of 3-(N-tert-butoxycarbonyl) aminopropanoic acid (822.0 mg, 4.34 mmol) and 4-methylmorpholine (442.0 mg, 4.37 mmol) in 14 mL of dry THF at −15° C. was added isobutylchloroformate (0.53 mL, 0.56 g, 4.1 mmol). The reaction mixture was stirred at −15° C. for 1 min followed by the addition of the amine from step C (1.72 g, 4.57 mmol). The reaction mixture was allowed to warm to 23° C. and was stirred for 1 h. The mixture was then filtered, the precipitate was washed with THF (5 mL) and the filtrate was concentrated in vacuo. The remaining material was partitioned between 2 N NaOH (50 mL) and $CH_2Cl_2$ (3×20 mL). The combined organic layers were dried over $Na_2SO_4$ and the solvent removed in vocuo to give 2.25 g of a brownish yellow gum. Purification of the crude material (2.25 g) by medium pressure liquid chromatography (silica gel, 1:1 $CHCl_3$/EtOAc) gave 627.0 mg (26%) of a pale yellow oil. $^1$H NMR: δ 3.63 (t, J=6.2 Hz, 4H), 3.54–3.35 (m, 4H), 3.20–3.19 (m, 2H), 2.71–2.50 (m, 6H), 1.43 (s, 9H), 0.89 (s, 18H), 0.05 (s, 12H). The amide and carbamate protons were not observed.

Step E β-Alanine, 2-(bis(2-tert-butyldimethylsilyloxyethyl) amino]ethyl amide

The protected amine formed in step D (627.0 mg, 1.14 mmol) was dissolved in trifluoroacetic acid (5 mL) at 23° C. The resulting solution was stirred for 5 min (until $CO_2$ evolution ceased) followed by removal of the trifluoroacetic acid in vacuo. The remaining material was partitioned between saturated $NaHCO_3$ (50 mL) and $CH_2Cl_2$ (3×20 mL). The combined organic layers were dried over $Na_2SO_4$ and the solvent removed in vacuo to give 203.4 mg (40%) of a pale yellow oil.

Step F β-Alanine, N-(acridin-9-yl), 2-[bis(2-tert-butyldimethylsilyloxyethyl)amino]ethyl amide A mixture of the crude amine from step E (203.4 mg, 0.45 mmol), 9-methoxyacridine (96.8 mg, 0.46 mmol) and methanol (10 mL) was heated to reflux for 4 h. The reaction mixture was allowed to cool to 23° C. and was stirred for an additional 2.5 days. The methanol was removed in vacuo and the remaining material was partitioned between 2 N NaOH (50 mL) and $CH_2Cl_2$ (3×20 mL). The combined organic layers were dried over $Na_2SO_4$ and the solvent removed in vacuo to give 69.6 mg of a yellow oil. Purification of the crude material (69.6 mg) by TLC (silica gel, 1:1 $CHCl_3$/EtOAC) gave 23.4 mg (8.3%) of a yellow oil. $^1$H NMR: δ 8.19 (d, J=8.8 Hz, 2H), 8.06 (d, J=8.8 Hz, 2H), 7.65 (br t, J=7.6 Hz, 2H), 7.36 (br t, J=7–6 Hz, 2H), 6.8–6.7 (m, 1H), 4.06 (t, J=5.6 Hz, 2H), 3.61 (t, J=5.8 Hz, 4H), 3.37–3.32 (m, 2H), 2.72–2.61 (m, 6H), 2.51 (t, J=5.5 Hz, 2H), 0.86 (s, 18H), 0.02 (s, 12H). The amine proton was not observed, $^{13}$C NMR: δ 172.1, 152.4, 149.3, 130.5, 129.3, 123.7, 118.0, 112.8, 62.3, 57.4, 54.1, 47,4, 38.2, 36.5, 26.4, 18.8, −4.8.

Step G β-Alanine, N-(acridin-9-yl), 2-[bis(2-hydroxyethyl) amino]ethyl amide dihydrochloride To a stirred solution of the bis-protected diol from step F (22.0 mg, 0.04 mmol) in isopropanol (1.0 mL) was added a 5–6 N HCl/isopropanol solution (0.05 mL) at 23° C. The reaction mixture was stirred at 23° C. for 17 h and the resultant yellow precipitate was collected by vacuum filtration. The yellow solid was rinsed with an additional 1.0 mL of isopropanol. Residual isopropanol was removed in vacuo (overnight) to give 11.4 mg (69%) of the diol dihydrochloride salt as a yellow solid. $^1$H NMR ($CD_3OD$): δ 8.52 (d, J=8.8 Hz, 2H), 7.96 (br t, J=7.5 Hz, 2H), 7.82 (d, J=8.4 Hz, 2H), 7.57 (br t, J=7.5 Hz, 2H), 4.49 (t, J=6.2 Hz, 2H), 3.91 (t, J=4.8 Hz, 4H), 3.74–3.56 (m, 2H), 3.53–3.38 (m, 6H), 2.97 (t, J=6.1 Hz, 2H). The amide, amine and hydroxyl protons were not observed.

Step H β-Alanine, N-(acridin-9-yl), 2-[bis(2-chloroethyl) amino]ethyl amide dihydrochloride To a stirred suspension of the diol from step G (11.4 mg, 0.024 mmol) in $CH_3CN$ (1.0 mL) was added $SOCL_2$ (0.12 mL, 200 mg, 1.7 mmol) at 23° C. The reaction mixture was stirred at 23° C. for 15 minutes and the solution was heated to 50° C. for 3.5 h. The resultant yellow precipitate was collected via vacuum filtration and was rinsed with $CH_3CN$ (3×1.0 mL) and dried in vacuo to give 8.3 mg (67%) of a yellow powder (95% pure by HPLC). $^1$H NMR ($CD_3OD$): δ 8.55 (d, J=8.7 Hz, 2H), 8.00(br t, J=7.7 Hz, 2H), 7.84 (d, J=8.7 Hz, 2H), 7.59 (br t, J=7.7 Hz, 2H), 4.51 (t, J=6.2 Hz, 2H), 3.98 (t, J=5.7 Hz, 4H), 3.71 (t, J=5.7 Hz, 4H), 3.65–3.55 (m, 2H), 3.55–3.42 (m, 2H), 2.99 (t, J=6.2 Hz, 2H). The amide and amine protons were not observed.

Example 8

Hydrolysis of the Frangible Compound

For the frangible compounds incorporating an ester group ("forward" and "reverse" esters) in the frangible linker, model compounds were studied to determine the amount of ester hydrolysis.

The reaction $$AcrNH—(CH_2)_n—C(=O)—OR \longrightarrow$$
("forward ester")

$$AcrNH—(CH_2)_n—CO_2H + HO—R$$
("acridine acid")

where AcrNH indicates a 9-amino acridine bearing substituents as indicated in the following table, and n and R are as indicated, was studied. Table III shows the rate enhancement for ester hydrolysis when the ester linkage is situated between, and in proximity to, an acridine ring and an alkylamino group. The hydrolysis rate is rapid regardless of whether the acridine moiety is positioned at the acid terminus of the ester, or at the alcohol terminus.

TABLE III

| | | Percent Hydrolysis at 100 minutes (aqueous solution, pH 8, 37° C.) | | |
|---|---|---|---|---|
| Acridine Substituent(s) | n = | R = methyl | R = —$(CH_2)_2N(CH_2CH_2OH)_2$ | R = —$(CH_2)_3N(CH_2CH_2OH)_2$ |
| 6-Cl, 2-OMe | 1 | 28% | | |
| 6-Cl, 2-OMe | 2 | 22% | | |
| 6-Cl, 2-OMe | 3 | 5% | | |
| 6-Cl, 2-OMe | 4 | 2% | | |
| 6-Cl, 2-OMe | 7 | <1% | | |
| 2-$CO_2CH_3$ | 2 | 9% | 55% | 57% |
| 2-$CO_2CH_3$ | 3 | | 18% | |
| 2-$CO_2CH_3$ | 4 | | 17% | |

For the reaction $$AcrNH—(CH_2)_n—O—C(=O)—R \longrightarrow$$
("reverse ester")

$$AcrNH—(CH_2)_n—OH + HOC(=O)—R$$
("acridine alcohol")

where AcrNH indicates a 9-amino acridine bearing substituents as indicated in the following table, and n and R are as indicated, the following results were obtained:

TABLE IV

| | | Percent Hydrolysis at 100 minutes (aqueous solution, pH 8, 37° C.) | | |
|---|---|---|---|---|
| Acridine Substituent(s) | n = | R = methyl | R = —$(CH_2)_2N(CH_2CH_2OH)_2$ | R = —$(CH_2)_3N(CH_2CH_2OH)_2$ |
| 6-Cl, 2-OMe | 2 | 2% | 99% | |
| 6-Cl, 2-OMe | 3 | 2% | 65% | |

At pH 3, all compounds in Tables III and IV showed ≦1% hydrolysis at 100 min.

The mustard compounds cannot be evaluated in the same manner since multiple degradation pathways occur simultaneously. Nevertheless, when Compound VIII is incubated under the same conditions as in Tables III and IV, the acridine acid is the major product (≧95%) after long incubation times and 40% is formed at 100 minutes. This compares favorably to the table entry for the analogous diol (57% hydrolysis at 100 minutes).

It will be appreciated from the data in Tables III and IV that the hydrolysis rate of the ester linkage varies inversely with the length of the linker arm between the 9-aminoacridine moiety and the ester group (in Tables III and IV, as n increases, the amount of hydrolysis at 100 minutes decreases). This provides a method of tuning the hydrolysis rate of the compounds. This ability to tune the breakdown of the linker allows compound reactivity to be adjusted for various applications, as desired.

MATERIALS

The following materials were used in the following Examples:

While it is commercially available from Baxter Healthcare Corp., Deerfield, Ill., Adsol used in this and the following experiments was made by sterile filtering the following mixture: 22 g glucose, 9 g NaCl, 7.5 g mannitol, and 0.27 g adenine in 1 liter of distilled water.

Quinacrine mustard was obtained from Aldrich Chemical Co., St. Louis, Mo.

Whole blood was obtained from the Sacramento Blood Center (Sacramento Calif.).

Example 9

Inactivation of Vesicular Stomatitis Virus (VSV)

Stock solutions (typically 10–30 mM) of each compound are prepared by dissolving an appropriate amount of material in blood bank saline previously acidified with 2 mM $H_3PO_4$, then quickly frozen in 1 mL aliquots. At the time of use, aliquots are warmed to ≦10° C. and used within one hour.

For preparation of packed red blood cells (PRBC), whole blood, with measured Hct, is centrifuged at 3800 rpm for 6 min. Supernatant plasma is removed and measured. Adsol is added to provide PRBC with 60% Hct. Plasma concentration is 15–20%.

A VSV (stock solution, approx. $10^9$ pfu/mL, obtained from ATCC American Type Cell Culture, Rockville, Md.) is diluted 1:10 into tissue culture medium (DMEM with 10%

NCS) or into PBRC to provide the test medium which is aliquoted (1 mL) into 2 mL sterile o-ring tubes.

To each tube is added sufficient test compound solution to provide a test compound concentration of 10–300 μM. Each sample is quickly mixed by fully pipetting the mixture several times. Suspensions are incubated at ambient temperature for 4 h. Virus titer was ascertained following incubation of the treated medium in BHK (baby hamster kidney) host cells. PRBC was used directly rather than the supernatant alone. Virus kill was inversely proportional to the appearance of plaques in the cell cultures. The difference between the titer of the untreated test medium and that of a treated sample provides the log kill for the compound at that concentration. The detection limit is $10^{1.4}$ pfu/mL.

In tissue culture medium, quinacrine mustard (QM), and Compounds IV, VI, XI, VII, and VIII inactivated >3 logs of VSV at <50 μM test compound. Compound XII inactivated 2 logs at approx. 200 μM. This compound is believed to be particularly unstable with respect to ester hydrolysis. As indicated in the first entry in Example 8, Table IV, the corresponding diol compound (β-alanine, [N,N-bis(2-hydroxyethyl)], 2-[(6-chloro-2-methoxyacridin-9-yl)amino] ethyl ester) was 99% hydrolyzed after 100 minutes at pH 8, 37° C. It is likely that the mustard compound also underwent rapid hydrolysis. This illustrates the importance of the anchor moiety for directing the effector portion of the molecule to nucleic acid, and the importance of tuning the reactivity of the 9-aminoacridine class of compounds so that they are effective under conditions of actual use. Under the described inactivation protocol, hydrolysis of Compound XII is expected to be competitive with inactivation.

In PRBC, QM and Compounds IV, VI, VIII, V, and XIII inactivated >2 logs of VSV at <150 μM of test compound.

Example 10

Inactivation of *Yersinia enterocolitica*

PRBC and stock solutions were prepared as for VSV in Example 9.

Yersinia (California Department of Health Services, Microbial Disease Laboratory, Berkeley, Calif.) is cultured in LB-broth at 37° C. overnight on a shaker. A portion (10 mL) is centrifuged at 2500 rpm for 10 min in a 15 mL conical tube. The pellet is resuspended in 1 mL of Adsol to provide approx. $10^9$ bacteria/mL. To measure the titer, the optical density is measured of a 1:100 dilution in Adsol ($OD_{610}$=0.2 at $10^8$ bacterial/mL). The bacterial stock is then diluted 1:100 into saline or PRBC to provide the test medium which is aliquoted (1 mL) into 2 mL o-ring sterile tubes.

To each tube is added a sufficient amount of the test compound solution to provide a test compound concentration of 10–300 μM. Each sample is quickly mixed by fully pipetting the mixture several times. It is then incubated for two hours at ambient temperature, then plated out on LB-agar starting with 100 μL sample starting at $10^{-1}$ dilution and continuing dilutions to $10^{-8}$. The plates are incubated overnight at 37° C. and the colonies are counted. The difference between the titer of the untreated test medium and that of a treated sample provides the log kill for the compound at that concentration. The detection limit is 10 bacteria/mL.

In saline, quinacrine mustard (QM) and Compounds IV, VI, VIII, V, IX, and X inactivated >2 logs of Yersinia at concentrations ≦200 μM.

In PRBC, QM and Compounds VI, VIII, V, X, and XIII inactivated >2 logs of Yersinia at concentrations ≦200 μM.

Example 11

Blood Function Assay After Introduction of a Compound of the Invention

One of the contemplated uses of the compounds of the invention involves the introduction of one or more of the compounds of the invention into blood or blood products intended for transfusion. The blood or blood product must remain suitable for transfusion after treatment with the compounds. To evaluate the effect of the compounds on red blood cell function, the compounds were tested as described below.

Packed red blood cells with a 50% hematocrit (Hct) is prepared by spinning whole blood with a known Hct at 2500 rpm for 6 min. The supernate is removed and measured. The suspension is diluted with a sufficient volume of Adsol to achieve the desired Hct.

1.5 mL of PRBC is placed in each 2 ml o-ring tube and enough of the stock solution of the test compound is added to achieve the desired concentration. The samples are incubated at ambient temperature for 4 hours, then stored overnight at 4° C. Hemolysis was determined as described in Hogman et al., Transfusion, 31:26–29 (1991).

A lysis standard is prepared for each sample by diluting 10 μM of the incubated mixture in two steps with water to give a final 1:4000 dilution.

For the assay, samples were removed from 4° C. storage and warmed for <15 minutes. After vortexing briefly to mix, an aliquot was removed and spun for 2 minutes at 14,000 rpm. The supernate was removed and spun for 10 minutes at 14,000 rpm. The supernate was removed and diluted as needed in water. The absorbance at 414 nm of the lysis standards and the diluted supernates were read against a water blank. Percent hemolysis was calculated as:

$$(100\%-50\%\ Hct)\times(A_{414}\ of\ sample\times dilution\ factor)/(A_{414}\ of\ lysis\ standard\times 4000)$$

The $A_{414}$ of the samples is uncorrected for any absorbance due to the presence of the compound of the invention. The results are given in Table Va.

TABLE Va

Hemolysis Data at Day 1

| Compound and Concentration | | Percent Hemolysis | Number of Samples Tested |
|---|---|---|---|
| BBS* | | 0.066 | 14 |
| ABBS** | | 0.065 | 8 |
| 150 μM QM*** | | 0.220 | 14 |
| 300 μM QM | | 0.320 | 14 |
| 150 μM | IV | 0.091 | 14 |
| 300 μM | IV | 0.109 | 14 |
| 150 μM | VI | 0.103 | 14 |
| 300 μM | VI | 0.140 | 14 |
| 150 μM | VIII | 0.110 | 6 |
| 300 μM | VIII | 0.135 | 6 |
| 150 μM | V | 0.136 | 2 |
| 300 μM | V | 0.149 | 2 |
| 150 μM | IX | 0.116 | 2 |
| 300 μM | IX | 0.099 | 2 |
| 150 μM | X | 0.121 | 2 |
| 300 μM | X | 0.153 | 2 |

*BBS = blood bank saline
**ABBS = acidic blood bank saline
***QM = quinacrine mustard Extracellular potassium was measured using a Ciba Corning Model 614 $K^+/Na^{30}$ Analyzer (Ciba Corning Diagnostics Corp., Medford, Mass.). ATP was measured using Sigma procedures No. 366 (Sigma, St. Louis, Mo.).

Table Vb. shows the relative values of extracellular potassium relative to the control values of the untreated PRBC samples for that experiment. For example, a relative value of 1.03 meant that the treated sample has 3% more extracellular potassium concentration than the untreated control.

TABLE Vb

Relative Extracellular Potassium Levels (replicates)*

| Compound | Concentration ($\mu$M) | Day 1 | Day 7 | Day 14 |
|---|---|---|---|---|
| IV | 100 | 1.01 (1) | 0.98 (1) | 1.03 (1) |
| | 200 | 1.05 (1) | 1.15 (1) | 1.01 (1) |
| | 300 | 1.03 (1) | 1.15 (1) | 1.15 (1) |
| V | 300 | 1.04–1.46 (4) | 0.96–1.01 (4) | 0.95–1.01 (4) |

*[K+] (treated)/[K+] (untreated)

Table Vc. shows the relative values ATP relative to the control values of the untreated PRBC samples for that experiment. For example, a relative value of 1.03 meant that the treated sample has 3% more ATP than the untreated control.

TABLE Vc

Relative ATP Levels (replicates)*

| Compound | Concentration ($\mu$M) | Day 1 | Day 7 | Day 14 |
|---|---|---|---|---|
| IV | 100 | 1.01 (1) | 0.93 (1) | 0.94 (1) |
| | 200 | 1.05 (1) | 0.94 (1) | 0.94 (1) |
| | 300 | 1.03 (1) | 0.93 (1) | 0.92 (1) |
| V | 300 | 0.96–100 (4) | 0.91–1.01 (4) | 0.94–1.01 (4) |

*[ATP] (treated)/[ATP] (untreated)

Example 12

Inactivation of HIV by Compounds of the Invention

Cell associated HIV in TC Medium (Popovic et al., *Science,* 224:497 (1984): H9-IIIb cells are suspended in TC Medium to provide a suspension with a titer of approximately ≦$10^6$ pfu/mL. To 2 mL aliquots of the test medium in 15 mL conical tubes is added a sufficient amount of test compound solution to achieve the desired concentration of active material. The suspensions are immediately mixed by fully pipetting several times, then vortexing briefly. The samples are incubated at ambient temperature for 2–4 h, then centrifuged. The pellets are resuspended in 1 mL of plaque assay diluent, then quickly frozen at −80° C. and titrated by a microplaque assay. (Hanson et al., J. Clin. Micro., 28:2030 (1990)).

Compounds quinacrine mustard, IV and VI inactivated >3 logs of HIV at ≦25 $\mu$M of test compound.

Cell-associated HIV in PRBC: For assays run in PRBC, the packed cells are prepared as described in the VSV assay. The HIV9-IIIb cells are added to the Adsol prior to dilution of the centrifuged cells. The resultant suspension is mixed by fully pipetting all the material. Upon completion of incubation of the test compound, the samples are diluted with 3 mL of a 1:1 plasma:DMEM solution containing 5 $\mu$L of heparin. The infected cells are then isolated using a fycol-hypaque gradient, resuspended in 1 mL of the diluent, and frozen for later titration.

Compounds quinacrine mustard, VI and V inactivated >3 logs of HIV at ≦200 $\mu$M of test compound.

Cell-free HIV in PRBC: The protocol is similar to that described above, except that cell-free HIV is added directly to the PRBC after preparation. After incubation, the medium is centrifuged and the supernate is frozen for later titration.

Compounds quinacrine mustard, IV, V and VI inactivated >3 logs of HIV at ≦100 $\mu$M of test compound.

Although the forgoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims. The entirety of U.S. Pat. Nos. 5,559,250 and 5,399,719 are hereby incorporated by reference. All other patents and references cited herein are hereby incorporated by reference.

What is claimed is:

1. A compound selected from the group consisting of:

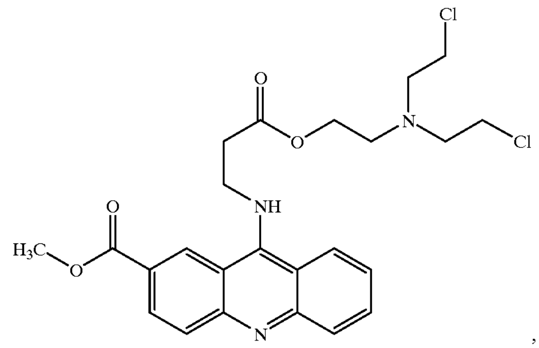

,

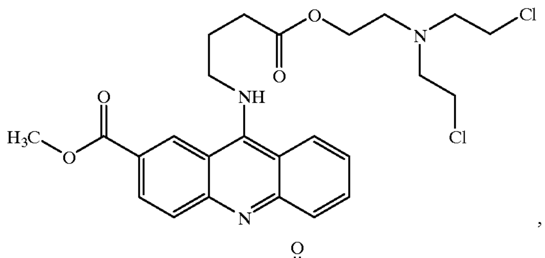

,

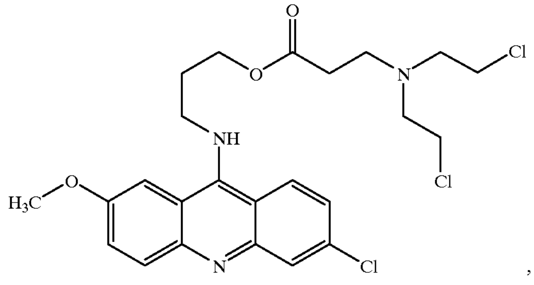

,

-continued
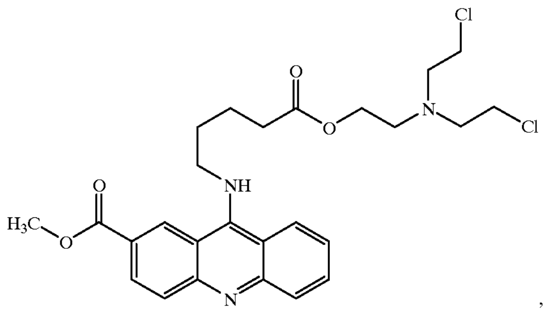
,
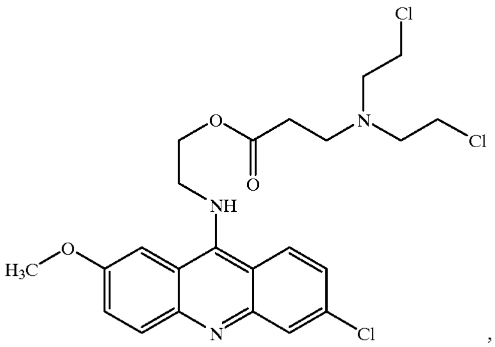
,
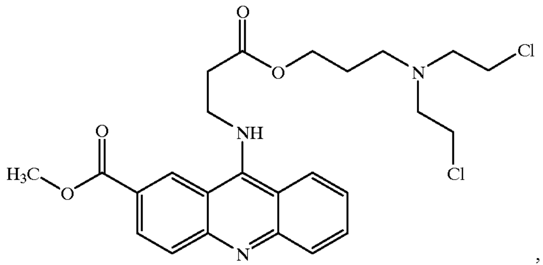
,
and
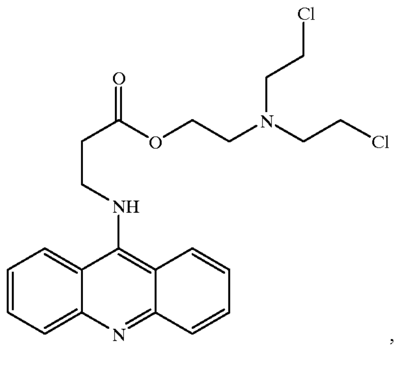
,
and all salts thereof.
2. A compound having the formula:
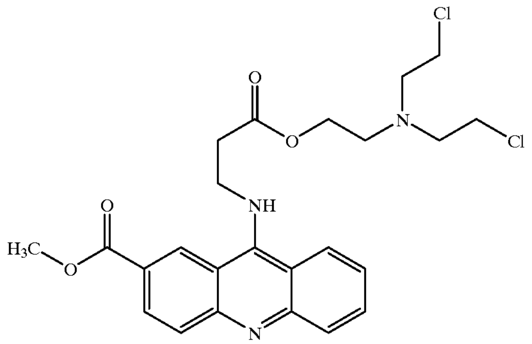
and all salts thereof.
3. A compound having the formula:
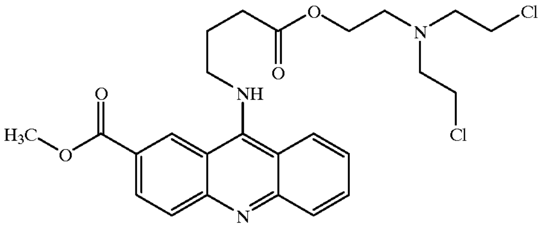
and all salts thereof.
4. A compound having the formula:
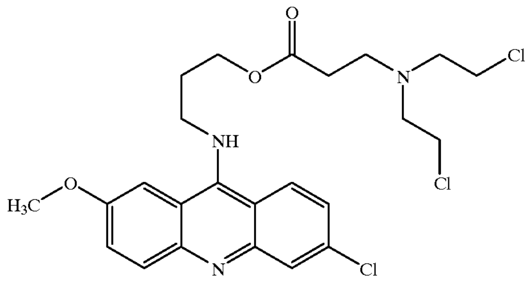
and all salts thereof.
5. A compound having the formula:
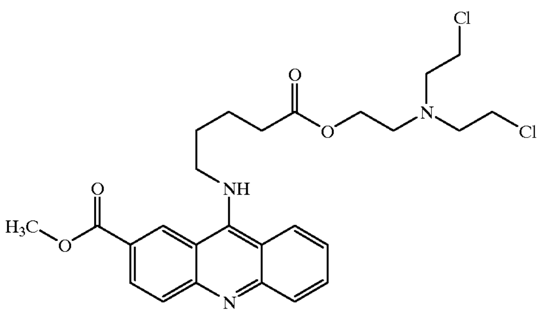
and all salts thereof.

6. A compound having the formula:

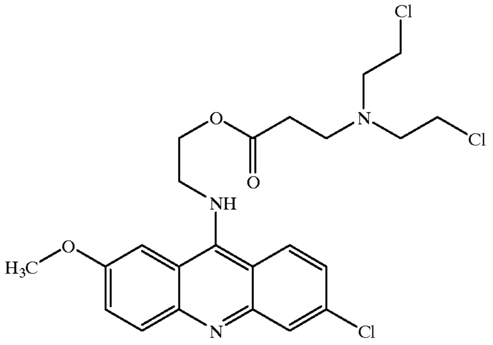

and all salts thereof.

7. A compound having the formula:

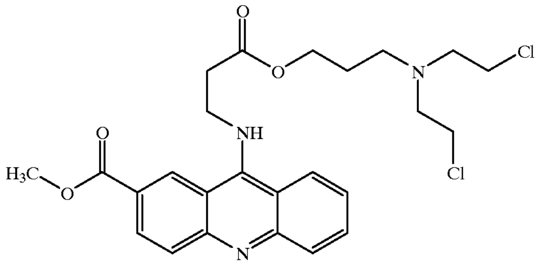

and all salts thereof.

8. A method of making a compound of claim 1, wherein the method comprises the step of reacting an amino ester with a 9-substituted acridine to provide an N-(9-acridinyl) amino ester.

9. A method according to claim 8, wherein the amino ester is an ω-amino alkanoic ester.

10. A method according to claim 8, wherein the amino ester is a β-alanine derivative.

11. A method according to claim 8, wherein the amino ester comprises a protected diol.

12. A method according to claim 11, further comprising the step of deprotecting the protected diol substituent to form an N-(9-acridinyl)amino ester comprising a diol substituent.

13. A method according to claim 8, wherein the amino ester comprises a protected bis(hydroxyalkyl)amine.

14. A method according to claim 8, wherein the 9-substituted acridine is a 9-methoxy acridine.

15. A method according to claim 8, wherein the 9-substituted acridine is a 9-chloro acridine.

16. A method according to claim 8, further comprising the step of converting the N-(9-acridinyl)amino ester into an N-(9-acridinyl)amino ester comprising a diol substituent.

17. A method according to claim 16, wherein the step of converting the N-(9-acridinyl)amino ester into an N-(9-acridinyl)amino ester comprising a diol substituent comprises a transesterification reaction.

18. A method according to claim 16, wherein the method further comprises the step of replacing the hydroxyl groups of the diol substituent with chloro groups.

19. A compound having the formula

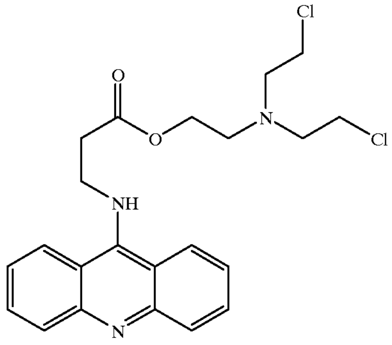

and all salts thereof.

20. A method for inactivating pathogens in a material, comprising:

adding a compound according to claim 1 to the material; and incubating said material.

21. A method according to claim 20, wherein the compound is added to the material to form a final solution having a concentration of the compound of between 1 and 500 μM.

22. A method according to claim 20, wherein the material is a biological material.

23. A method according to claim 22, wherein the biological material comprises a composition selected from the group consisting of blood, blood products, plasma, platelet preparations, red blood cells, packed red blood cells, serum, sweat, cerebrospinal fluid, saliva, urine, feces, semen, milk, tissue samples, homogenized tissue samples, cell culture medium, cell cultures, viral cultures, and cultures incorporating material derived from a living organism.

24. A method according to claim 22, wherein the material comprises a blood product.

25. A method according to claim 22, wherein the material comprises red blood cells.

26. A method according to claim 20, wherein the method comprises adding the compound to the material in an effective amount to inactivate at least about 2 logs of a pathogen in the material.

27. A method according to claim 20, wherein the time of incubation is at least about 1 to 48 hours.

28. A method for inactivating pathogens in a material, comprising:

adding a compound according to claim 19 to the material; and incubating said material.

29. A method according to claim 28, wherein the compound is added to the material to form a final solution having a concentration of the compound of between 1 and 500 μM.

30. A method according to claim 28, wherein the material is a biological material.

31. A method according to claim 30, wherein the biological material comprises a composition selected from the group consisting of blood, blood products, plasma, platelet preparations, red blood cells, packed red blood cells, serum, sweat, cerebrospinal fluid, saliva, urine, feces, semen, milk, tissue samples, homogenized tissue samples, cell culture medium, cell cultures, viral cultures, and cultures incorporating material derived from a living organism.

32. A method according to claim 30, wherein the material comprises a blood product.

33. A method according to claim 30, wherein the material comprises red blood cells.

34. A method according to claim 28, wherein the method comprises adding the compound to the material in an effective amount to inactivate at least about 2 logs of a pathogen in the material.

35. A method according to claim 28, wherein the time of incubation is at least about 1 to 48 hours.

36. A method of making a compound of claim 19, wherein the method comprises the step of reacting an amino ester with a 9-substituted acridine to provide an N-(9-acridinyl) amino ester.

37. A method according to claim 36, wherein the amino ester is an ω-amino alkanoic ester.

38. A method according to claim 36, wherein the amino ester is a β-alanine derivative.

39. A method according to claim 36, wherein the amino ester comprises a protected diol.

40. A method according to claim 39, further comprising the step of deprotecting the protected diol substituent to form an N-(9-acridinyl)amino ester comprising a diol substituent.

41. A method according to claim 36, wherein the amino ester comprises a protected bis(hydroxyalkyl)amine.

42. A method according to claim 36, wherein the 9-substituted acridine is a 9-methoxy acridine.

43. A method according to claim 36, wherein the 9-substituted acridine is a 9-chloro acridine.

44. A method according to claim 36, further comprising the step of converting the N-(9-acridinyl)amino ester into an N-(9-acridinyl)amino ester comprising a diol substituent.

45. A method according to claim 44, wherein the step of converting the N-(9-acridinyl)amino ester into an N-(9-acridinyl)amino ester comprising a diol substituent comprises a transesterification reaction.

46. A method according to claim 44, wherein the method further comprises the step of replacing the hydroxyl groups of the diol substituent with chloro groups.

* * * * *

UNITED STATES PATENT AND TRADEMARK OFFICE

CERTIFICATE OF CORRECTION

PATENT NO. : 6,093,725
DATED : July 25, 2000
INVENTOR(S) : David Cook et al.

It is certified that error appears in the above-identified patent and that said Letters Patent is hereby corrected as shown below:

Title page,
Item [75], Inventors, please add the name of -- William A. Denny -- as an inventor.

Signed and Sealed this

Thirty-first Day of December, 2002

JAMES E. ROGAN
*Director of the United States Patent and Trademark Office*